US012104000B2

(12) United States Patent
Abuelyaman et al.

(10) Patent No.: US 12,104,000 B2
(45) Date of Patent: Oct. 1, 2024

(54) PHOTOPOLYMERIZABLE COMPOSITIONS INCLUDING A POLYPROPYLENE OXIDE COMPONENT, ARTICLES, AND METHODS

(71) Applicant: 3M INNOVATIVE PROPERTIES COMPANY, St. Paul, MN (US)

(72) Inventors: Ahmed S. Abuelyaman, Woodbury, MN (US); Zeba Parkar, Marietta, GA (US); John M. Riedesel, San Jose, CA (US)

(73) Assignee: Solventum Intellectual Properties Company, Maplewood, MN (US)

( * ) Notice: Subject to any disclaimer, the term of this patent is extended or adjusted under 35 U.S.C. 154(b) by 894 days.

(21) Appl. No.: 16/960,566

(22) PCT Filed: Mar. 6, 2019

(86) PCT No.: PCT/IB2019/051815
§ 371 (c)(1),
(2) Date: Jul. 8, 2020

(87) PCT Pub. No.: WO2019/175716
PCT Pub. Date: Sep. 19, 2019

(65) Prior Publication Data
US 2020/0332046 A1     Oct. 22, 2020

Related U.S. Application Data

(60) Provisional application No. 62/643,431, filed on Mar. 15, 2018.

(51) Int. Cl.
| | |
|---|---|
| *C08F 299/02* | (2006.01) |
| *B29C 64/135* | (2017.01) |
| *B33Y 10/00* | (2015.01) |
| *B33Y 30/00* | (2015.01) |
| *B33Y 70/00* | (2020.01) |
| *C07C 69/54* | (2006.01) |
| *C07C 271/22* | (2006.01) |
| *C08F 2/46* | (2006.01) |
| *C08F 2/50* | (2006.01) |
| *C08G 61/04* | (2006.01) |
| *B29C 64/393* | (2017.01) |
| *B29K 71/00* | (2006.01) |
| *B33Y 50/02* | (2015.01) |

(52) U.S. Cl.
CPC ........ *C08F 299/024* (2013.01); *B29C 64/135* (2017.08); *B33Y 10/00* (2014.12); *B33Y 30/00* (2014.12); *B33Y 70/00* (2014.12); *C07C 69/54* (2013.01); *C07C 271/22* (2013.01); *B29C 64/393* (2017.08); *B29K 2071/02* (2013.01); *B33Y 50/02* (2014.12)

(58) Field of Classification Search
CPC ......... B33Y 30/00; B33Y 80/00; B33Y 10/00; B33Y 70/00; B33Y 50/02; C07C 271/22; C07C 69/54; B29C 64/135; B29C 64/393; A61C 7/08; C08F 299/024; A61K 6/887; C08L 33/10; B29K 2071/02
USPC ........ 524/523, 515, 502, 500, 1; 522/6, 189, 522/184, 71, 1; 520/1
See application file for complete search history.

(56) References Cited

U.S. PATENT DOCUMENTS

| | | | |
|---|---|---|---|
| 3,429,722 | A | 2/1969 | Economy |
| 3,795,524 | A | 3/1974 | Sowman |
| 4,047,965 | A | 9/1977 | Karst |
| 4,642,126 | A | 2/1987 | Zador |

(Continued)

FOREIGN PATENT DOCUMENTS

| | | |
|---|---|---|
| CN | 105440988 | 3/2016 |
| CN | 109016496 A | 12/2018 |

(Continued)

OTHER PUBLICATIONS

Kurashige et al, JP 2011221256 Machine Translation, Nov. 4, 2011 (Year: 2011).*
Cavex LC Dental Tray, Apr. 2015, 6 pages.
EBECRYL® 8808 Aliphatic Urethane Diacrylate, Allnex Technical Data Sheet, 2013, 2 pages.
MAPPES, Types of Orthodontic Appliances, 6 pages.
Speckhard, "Properties of UV Curable Polyurethane Acrylates", Department of Chemical Engineering, 1984, pp. 522-525.
International Search Report for PCT International Application No. PCT/IB2019/051815, mailed on Jun. 18, 2019, 3 pages.
Tsay, "The Synthesis and Properties of UV-Curable Urethane Acrylate Oligomer", Journal of National Cheng-Kung University, 1988, vol. 23, pp. 63-77.

*Primary Examiner* — Jessica Whiteley

(57) ABSTRACT

The present disclosure provides a photopolymerizable composition. The photopolymerizable composition includes at least one polypropylene oxide component and an initiator, plus optionally a urethane component, a multifunctional reactive diluent, and/or an inhibitor. The present disclosure also provides an article including the reaction product of the photopolymerizable composition. Typically, the article exhibits an elongation at break of 30% or greater. Further, the present disclosure provides a method of making an article. The method includes (i) providing a photopolymerizable composition and (ii) selectively curing the photopolymerizable composition to form an article. The method optionally also includes (iii) curing unpolymerized polypropylene oxide component, urethane component and/or multifunctional reactive diluent remaining after step (ii). Further, methods are provided, including receiving, by a manufacturing device having one or more processors, a digital object comprising data specifying an article; and generating, with the manufacturing device by an additive manufacturing process, the article based on the digital object. A system is also provided, including a display that displays a 3D model of an article; and one or more processors that, in response to the 3D model selected by a user, cause a 3D printer to create a physical object of an article.

20 Claims, 7 Drawing Sheets

(56) References Cited

U.S. PATENT DOCUMENTS

| | | | |
|---|---|---|---|
| 4,652,274 | A | 3/1987 | Boettcher |
| 4,867,680 | A | 9/1989 | Hare |
| 4,954,462 | A | 9/1990 | Wood |
| 4,978,391 | A | 12/1990 | Jones |
| 5,177,120 | A | 1/1993 | Hare |
| 5,185,299 | A | 2/1993 | Wood |
| 5,780,154 | A | 7/1998 | Okano |
| 5,863,486 | A | 1/1999 | Ozaki et al. |
| 5,981,621 | A | 11/1999 | Clark |
| 6,017,973 | A | 1/2000 | Tamura |
| 6,183,593 | B1 | 2/2001 | Narang |
| 6,200,732 | B1 | 3/2001 | Tamura |
| 6,399,278 | B1 | 6/2002 | Leach |
| 8,329,776 | B2 | 12/2012 | Hecht |
| 9,205,601 | B2 | 12/2015 | DeSimone |
| 9,295,617 | B2 | 3/2016 | Eckert |
| 9,360,757 | B2 | 6/2016 | DeSimone |
| 9,387,056 | B2 | 7/2016 | Wachter |
| 11,225,535 | B2 | 1/2022 | Klun et al. |
| 11,708,428 | B2 | 7/2023 | Klun |
| 2007/0031791 | A1 | 2/2007 | Cinader, Jr. |
| 2008/0248442 | A1 | 10/2008 | Raby |
| 2010/0197824 | A1 | 8/2010 | Bissinger |
| 2011/0091832 | A1 | 4/2011 | Kim |
| 2012/0046376 | A1 | 2/2012 | Loccufier |
| 2012/0088090 | A1 | 4/2012 | Miyazaki |
| 2013/0078594 | A1 | 3/2013 | Leslie-Martin |
| 2013/0095446 | A1 | 4/2013 | Andreiko |
| 2014/0356799 | A1 | 12/2014 | Cinader, Jr. |
| 2016/0311163 | A1 | 10/2016 | Yasukochi |
| 2017/0007362 | A1 | 1/2017 | Chen |
| 2017/0367792 | A1 | 12/2017 | Raby |
| 2019/0374309 | A1 | 12/2019 | Parkar |
| 2021/0315668 | A1 | 10/2021 | Achten |

FOREIGN PATENT DOCUMENTS

| | | | |
|---|---|---|---|
| EP | 0142172 | A2 | 5/1985 |
| EP | 0 476 789 | | 3/1992 |
| EP | 0 493 320 | A2 | 7/1992 |
| EP | 0562826 | A1 | 9/1993 |
| EP | 2008636 | | 12/2008 |
| EP | 2167013 | | 3/2010 |
| EP | 2 842 980 | | 3/2015 |
| EP | 3040046 | A1 | 7/2016 |
| JP | H 08-323867 | A | 12/1996 |
| JP | 2000085018 | A | 3/2000 |
| JP | 2001-302744 | | 10/2001 |
| JP | 2001-310918 | | 11/2011 |
| JP | 2011221256 | A * | 11/2011 |
| JP | 2013-170215 | A | 9/2013 |
| JP | 2014031453 | | 2/2014 |
| JP | 2014227453 | A * | 12/2014 |
| WO | WO 1996-15179 | | 5/1996 |
| WO | WO 2006-044012 | | 4/2006 |
| WO | WO 2009-045752 | | 4/2009 |
| WO | WO 2013/052105 | | 4/2013 |
| WO | 2014077688 | A1 | 5/2014 |
| WO | WO 2014-078537 | | 5/2014 |
| WO | WO 2014-098956 | | 6/2014 |
| WO | WO 2015-094842 | | 6/2015 |
| WO | WO 2015-182697 | | 12/2015 |
| WO | WO 2015-200201 | | 12/2015 |
| WO | WO 2016-071811 | | 5/2016 |
| WO | WO 2016-109660 | | 7/2016 |
| WO | WO 2016-148960 | | 9/2016 |
| WO | WO 2016-149007 | | 9/2016 |
| WO | WO 2016-187155 | | 11/2016 |
| WO | WO 2017-171490 | | 10/2017 |
| WO | WO 2018-005501 | | 1/2018 |
| WO | WO 2019-023009 | | 1/2019 |
| WO | WO 2019-103855 | | 5/2019 |

* cited by examiner

PHOTOPOLYMERIZABLE COMPOSITIONS INCLUDING A POLYPROPYLENE OXIDE COMPONENT, ARTICLES, AND METHODS

CROSS REFERENCE TO RELATED APPLICATIONS

This application is a national stage filing under 35 U.S.C. 371 of PCT/IB2019/051815, filed Mar. 6, 2019, which claims the benefit of U.S. Application No. 62/643,431, filed Mar. 15, 2018, the disclosure of which is incorporated by reference in its/their entirety herein.

TECHNICAL FIELD

The present disclosure broadly relates to articles including a polypropylene oxide component, and methods of making the articles, such as additive manufacturing methods.

BACKGROUND

The use of stereolithography and inkjet printing to produce three-dimensional articles has been known for a relatively long time, and these processes are generally known as methods of so called 3D printing (or additive manufacturing). In vat polymerization techniques (of which stereolithography is one type), the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is often not yet fully cured and must, usually, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

SUMMARY

Existing printable/polymerizable resins tend to be too brittle (e.g., low elongation, short-chain crosslinked bonds, thermoset composition, and/or high glass transition temperature) for a resilient oral appliance such as an aligner. An aligner or other appliance prepared from such resins could easily break in the patient's mouth during treatment, creating material fragments that may abrade or puncture exposed tissue or be swallowed. These fractures at the very least interrupt treatment and could have serious health consequences for the patient. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in both the final cured article. In contrast, compositions for inkjet printing processes need to be much lower viscosity to be able to jetted through nozzles, which is not the case for most vat polymerization resins.

Urethane (meth)acrylates are a class of raw materials that have interesting properties, for example an elongation of over 100% when cured, and very high toughness. But these resins also have a very high viscosity; at room temperature they are basically solids. Therefore, they only have been used in small amounts in photosensitive resin formulations for vat polymerization or stereolithography, and the properties of these resins are dominated by the other components.

In a first aspect, a photopolymerizable composition is provided. The photopolymerizable composition includes a blend of (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a second aspect, an article is provided. The article includes a reaction product of a photopolymerizable composition according to the first aspect. Typically, the article exhibits an elongation at break of 30% or greater.

In a third aspect, a method of making an article is provided. The method includes (a) providing a photopolymerizable composition according to the first aspect; (b) selectively curing the photopolymerizable composition to form an article; and optionally curing unpolymerized urethane component, polypropylene oxide component, and/or reactive diluent remaining after step (b).

In a fourth aspect, a non-transitory machine readable medium is provided. The non-transitory machine readable medium includes data representing a three-dimensional model of an article, when accessed by one or more processors interfacing with a 3D printer, causes the 3D printer to create an article comprising a reaction product of a photopolymerizable composition according to the first aspect.

In a fifth aspect, a method is provided. The method includes (a) retrieving, from a non-transitory machine readable medium, data representing a 3D model of an article; (b) executing, by one or more processors, a 3D printing application interfacing with a manufacturing device using the data; and c) generating, by the manufacturing device, a physical object of the article, the article comprising a reaction product of a photopolymerizable composition according to the first aspect.

In a sixth aspect, another method is provided. The method includes (a) receiving, by a manufacturing device having one or more processors, a digital object comprising data specifying a plurality of layers of an article; and (b) generating, with the manufacturing device by an additive manufacturing process, the article based on the digital object, the article comprising a reaction product of a photopolymerizable composition according to the first aspect.

In a seventh aspect, a system is provided. The system includes a display that displays a 3D model of an article; and one or more processors that, in response to the 3D model selected by a user, cause a 3D printer to create a physical object of an article, the article comprising a reaction product of a photopolymerizable composition according to the first aspect.

Clear tray aligners and tensile bars made according to at least certain embodiments of this disclosure were found to show low brittleness, good resistance to water, and good toughness.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
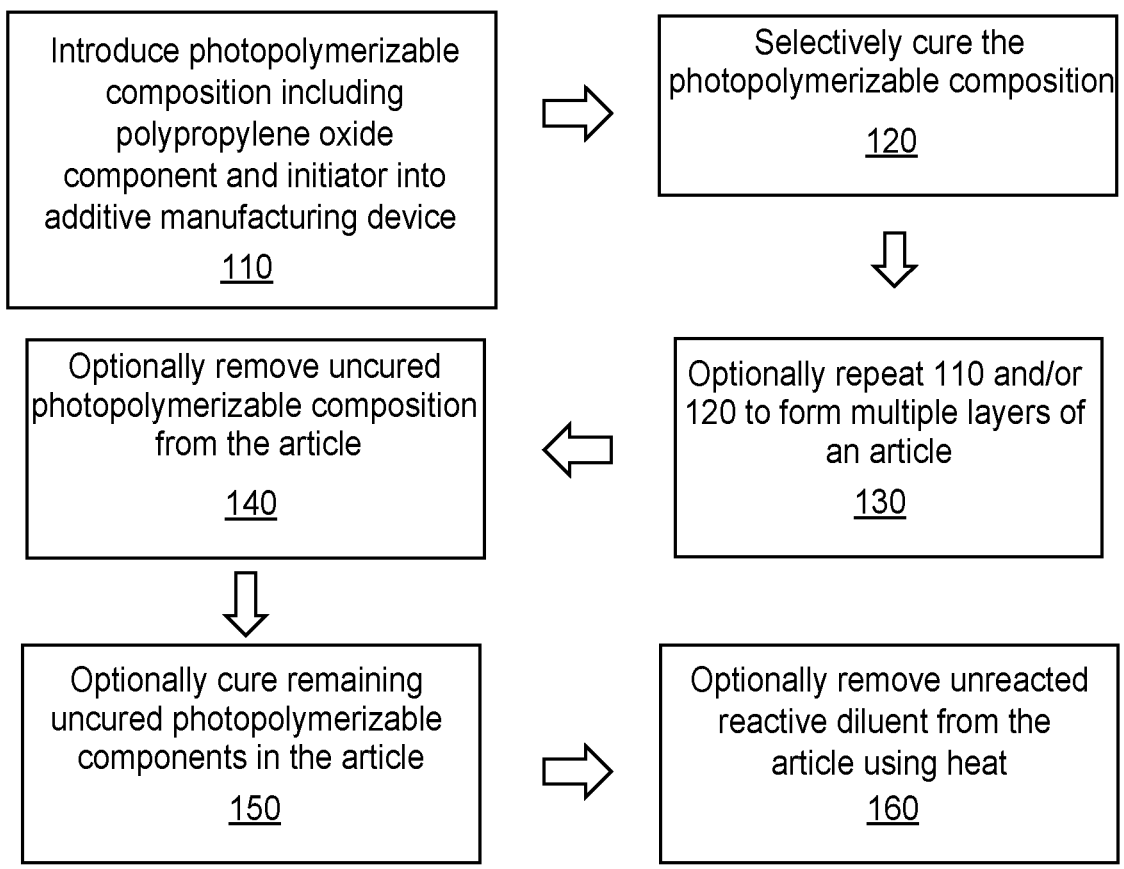
FIG. 1 is a flowchart of a process for building an article using the photopolymerizable compositions disclosed herein.

While the above-identified figures set forth several embodiments of the disclosure other embodiments are also contemplated, as noted in the description. The figures are not necessary drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, "aliphatic group" means a saturated or unsaturated linear, branched, or cyclic hydrocarbon group. This term is used to encompass alkyl, alkenyl, and alkynyl groups, for example.

As used herein, "alkyl" means a linear or branched, cyclic or acyclic, saturated monovalent hydrocarbon having from one to thirty-two carbon atoms, e.g., methyl, ethyl, 1-propyl, 2-propyl, pentyl, and the like.

As used herein, "alkylene" means a linear saturated divalent hydrocarbon having from one to twelve carbon atoms or a branched saturated divalent hydrocarbon radical having from three to twelve carbon atoms, e.g., methylene, ethylene, propylene, 2-methylpropylene, pentylene, hexylene, and the like.

As used herein, "alkenyl" refers to a monovalent linear or branched unsaturated aliphatic group with one or more carbon-carbon double bonds, e.g., vinyl. Unless otherwise indicated, the alkenyl groups typically contain from one to twenty carbon atoms.

As used herein, "alkenediyl" refers to a straight-chained, branched, or cyclic divalent unsaturated aliphatic group, e.g., —CH=CH—, —CH=C(CH$_3$)CH$_2$—, —CH=CHCH$_2$—, and the like.

Unless otherwise indicated, the alkenediyl groups typically contain from one to twenty carbon atoms.

As used herein, "heteroalkyl" refers to a straight-chained, branched, or cyclic alkyl group with one or more heteroatoms independently selected from N, O, and S, preferably N or O, including both unsubstituted and substituted alkyl groups. Unless otherwise indicated, the heteroalkyl groups typically contain from one to twenty carbon atoms and one or more N, O, or S atoms. Examples of "heteroalkyl" as used herein include, but are not limited to, methoxy, ethoxy, propoxy, 3,6-dioxaheptyl, 4-dimethylaminobutyl, and the like. Unless otherwise noted, heteroalkyl groups may be mono- or polyvalent, i.e. monovalent heteroalkyl or polyvalent heteroalkylene. "Heteroalkenyl" refers to a monovalent linear or branched unsaturated aliphatic group with one or more carbon-carbon double bonds including one or more heteroatoms independently selected from N, O, and S, preferably N or O, with both unsubstituted and substituted aliphatic groups. "Heteroalkenediyl" refers to a straight-chained, branched, or cyclic divalent unsaturated aliphatic group including one or more heteroatoms independently selected from N, O. and S, preferably N or O including both unsubstituted and substituted aliphatic groups.

As used herein, the terms "hardenable" refers to a material that can be cured or solidified, e.g., by heating to remove solvent, heating to cause polymerization, chemical cross-linking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, "(meth)acrylic" is a shorthand reference to acrylic, methacrylic, or combinations thereof, and "(meth)acryl" is a shorthand reference to acryl and methacryl groups. "Acryl" refers to derivatives of acrylic acid, such as acrylates, methacrylates, acrylamides, and methacrylamides. By "(meth)acryl" is meant a monomer or oligomer having at least one acryl or methacryl groups, and linked by an aliphatic segment if containing two or more groups. As used herein, "(meth)acrylate-functional compounds" are compounds that include, among other things, a (meth)acrylate moiety.

As used herein, "non-crosslinkable" refers to a polymer that does not undergo crosslinking when exposed to actinic radiation or elevated heat. Typically, non-crosslinkable polymers are non-functionalized polymers such that they lack functional groups that would participate in crosslinking.

As used herein, "oligomer" refers to a molecule that has one or more properties that change upon the addition of a single further repeat unit.

As used herein, "polymer" refers to a molecule having one or more properties that do not change upon the addition of a single further repeat unit.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used.

As used herein, a "resin" contains all polymerizable components (monomers, oligomers and/or polymers) being present in a hardenable composition. The resin may contain only one polymerizable component compound or a mixture of different polymerizable compounds.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically cross-linked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, the present disclosure provides a photopolymerizable composition. A photopolymerizable composition comprising a blend of:

a. 1 to 80 wt. %, inclusive, of at least one polypropylene oxide component based on the total weight of the photopolymerizable composition, the polypropylene oxide component comprising i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof, b. optionally 30 wt. % or greater of at least one urethane component, if present, based on the total weight of the photopolymerizable composition; with the proviso that when the at least one urethane component is not present the at least one polypropylene oxide component comprises at least two functional groups selected from oxycarbonylamino, amino carbonyloxy, and combinations thereof, c. optionally at least one multifunctional reactive diluent in an amount of 1 to 30 wt. %, inclusive, if present, based on the total weight of the photopolymerizable composition;

d. 0.1 to 5 wt. %, inclusive, of at least one initiator; and e. an optional inhibitor in an amount of 0.001 to 1 wt. %, inclusive, if present, based on the total weight of the photopolymerizable composition.

The components (a) through (e) are discussed in detail below.

Polypropylene Oxide Component

The photopolymerizable compositions of the present disclosure include at least one polypropylene oxide component. As used herein, a "polypropylene oxide component" refers to a compound including one or more polypropylene glycol functionalities in the backbone of the compound or polymer. The polypropylene glycol functionality is of the following Formula A:

Various commercially available polypropylene oxide polyol materials are referred to by vendors as polypropylene glycol polyol materials. Polypropylene oxides can be prepared by the ring opening polymerization of propylene oxide, initiated by an alcohol and catalyzed by a base (e.g., potassium hydroxide).

In particular, the polypropylene oxide component according to the present disclosure comprises i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The presence of two (or more) (meth)acryl groups helps ensure that the polypropylene oxide component reacts with at least one other (and preferably two) components of the photopolymerizable composition such that it would not be unreacted and able to leach out of the polymerized product. When no urethane component is present in the photopolymerizable composition, the polypropylene oxide component comprises at least two functional groups selected from oxycarbonylamino, amino carbonyloxy, and combinations thereof. These functional groups act as linkers attaching the (meth)acryl groups to the polypropylene oxide segment. Often, the at least one polypropylene oxide component comprises at least two functional groups selected from oxycarbonylamino, oxycarbonyl, amino carbonyloxy, carbonyloxy, and combinations thereof.

The at least one polypropylene oxide component is cross-linkable and provides flexibility (e.g., at least a minimum elongation at break) to the final article, and when it contains oxycarbonylamino and/or amino carbonyloxy functional groups, also toughness (e.g., at least a minimum tensile strength and/or modulus) to the final article. It has been discovered that the polypropylene oxide component can provide an advantageously long chain length, which provides flexibility without crystallization of the polypropylene oxide component either by itself or within the photopolymerizable composition. Without wishing to be bound by theory, it is believed that pendant groups present on the polypropylene oxide component can disrupt a tendency of the polypropylene oxide component to crystallize.

Typically, the polypropylene oxide segment can have a molecular weight of 400 grams per mole (g/mol) or greater, 500 g/mol or greater, 600 g/mol or greater, 700 g/mol or greater, 800 g/mol or greater, 900 g/mol or greater, 1,000 g/mol or greater, 1,100 g/mol or greater, or 1,200 g/mol or greater; and 2,000 g/mol or less, 1,900 g/mol or less, 1,800 g/mol or less, 1,700 g/mol or less, 1,600 g/mol or less, 1,500 g/mol or less, 1,400 g/mol or less, or 1,300 g/mol or less. Stated another way, the polypropylene oxide segment can have a molecular weight of 400 g/mol to 2,000 g/mol, 400 g/mol to 1,300 g/mol, or 1,000 g/mol to 2,000 g/mol. It was found that a polypropylene oxide segment having a molecular weight of 4,000 g/mol, however, was too long to blend with the other components of the photopolymerizable composition. In contrast to the polypropylene oxide component, polyethylene glycol compounds of similar size (e.g., containing 14, 16, 18, or more carbon atoms) are solids.

In many embodiments, the polymerizable component can include at least one polypropylene oxide component of Formula I:

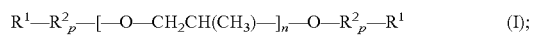

wherein n is an integer in a range of 5 to 70, inclusive (e.g., 5 to 60, 5 to 50, 5 to 40, 5 to 30, 5 to 20, 15 to 40, 15 to 30, or 15 to 20); $R^1$ is a monovalent group of Formula II:

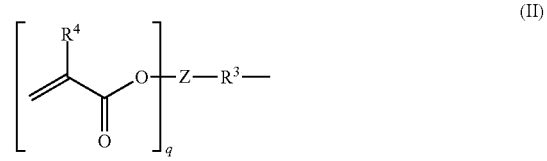

wherein $R^4$ is selected from H and $CH_3$; Z is a linking group with a valency of q+1, the linking group containing from 1 to 10 carbon atoms and optionally substituted by at least one of sulfur, nitrogen, and/or oxygen (e.g., examples of Z include linear, cyclic, and/or branched alkylene, with or without substitution of at least one carbon atom by an N, S, or O atom, sulfonyl group, nitro group, carbonyl group, or a combination thereof); q is 1 or 2; and $R^3$ is a divalent group of Formula III, Formula IV, Formula V, or Formula VI:

wherein R and $R^6$ are independently selected from an alkylene, a heteroalkylene, an alkenediyl, and a heteroalkenediyl;

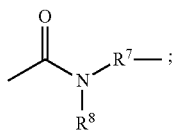
(IV)

wherein $R^7$ is an alkylene or an alkenediyl; and R is H, an alkyl, a heteroalkyl, an alkenyl, or a heteroalkenyl;

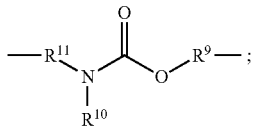
(V)

wherein $R^9$ and $R^{11}$ are independently selected from an alkylene, a heteroalkylene, an alkenediyl, and a heteroalkenediyl; and $R^{10}$ is H, an alkyl, a heteroalkyl, an alkenyl, or a heteroalkenyl; and

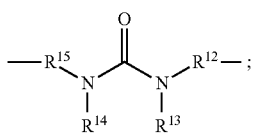
(VI)

wherein $R^{12}$ and $R^{13}$ are independently selected from an alkylene, a heteroalkylene, an alkenediyl, and a heteroalkenediyl; and $R^{13}$ and $R^{14}$ are independently selected from H, an alkyl, a heteroalkyl, an alkenyl, and a heteroalkenyl; p is 0 or 1; and R is of Formula III, Formula IV, Formula V, or Formula VI, wherein the R groups are as defined above for each of Formula III, Formula IV, Formula V, or Formula VI. In some select embodiments, p is 0, whereas in other select embodiments, p is 1.

For example, one suitable polypropylene oxide component is of Formula VII:

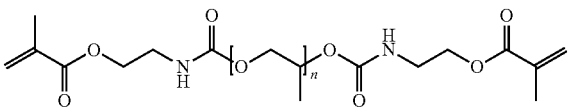
(VII)

wherein n is 5 to 70, 5 to 60, 5 to 50, 5 to 40, 5 to 30, or 5 to 20.

Another suitable polypropylene oxide component is of Formula VIII:

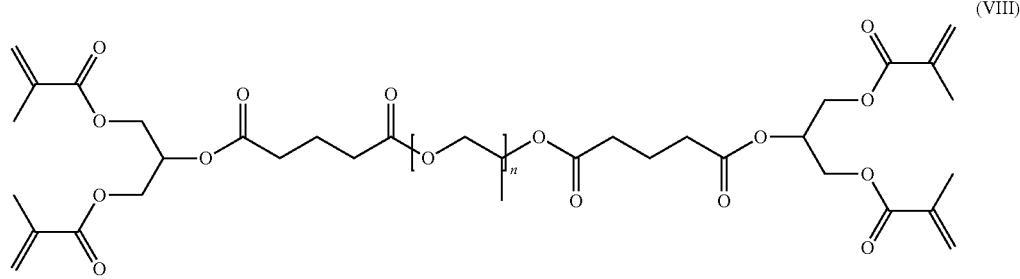
(VIII)

wherein n is 5 to 70, 5 to 60, 5 to 50, 5 to 40, 5 to 30, or 5 to 20.

A further suitable polypropylene oxide component is of Formula IX:

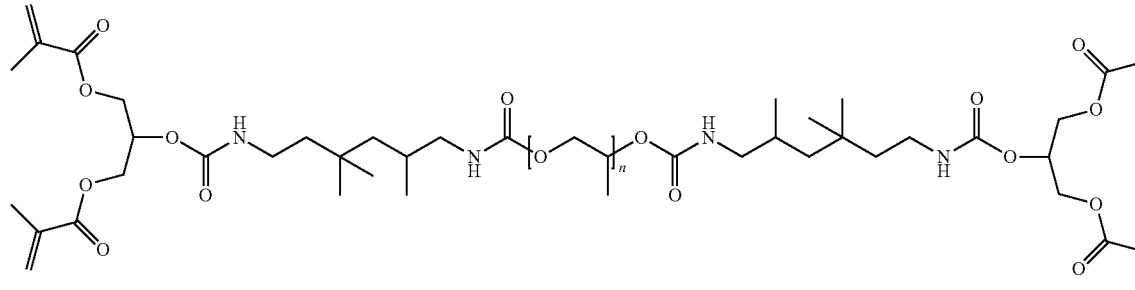
(IX)

wherein n is 5 to 70, 5 to 60, 5 to 50, 5 to 40, 5 to 30, 5 to 20, or 15 to 20.

An additional suitable polypropylene oxide component is of Formula X:

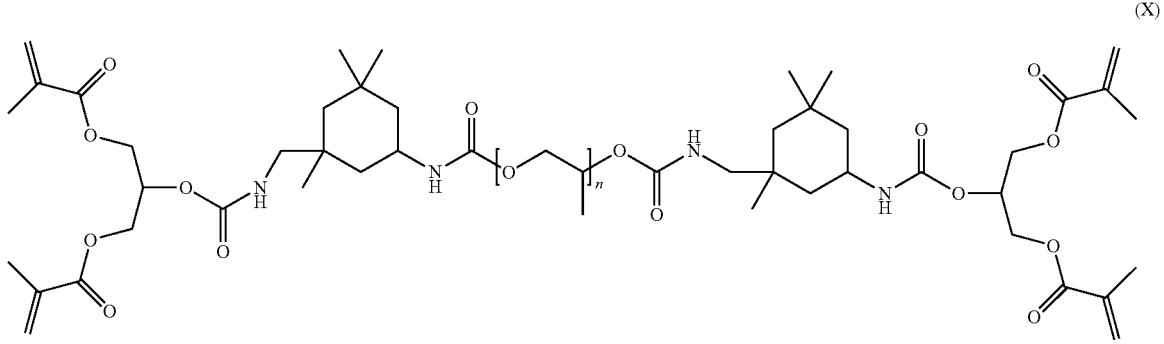

wherein n is 5 to 70, 5 to 60, 5 to 50, 5 to 40, 5 to 30, 5 to 20, or 15 to 20.

Yet another suitable polypropylene oxide component is of Formula XI:

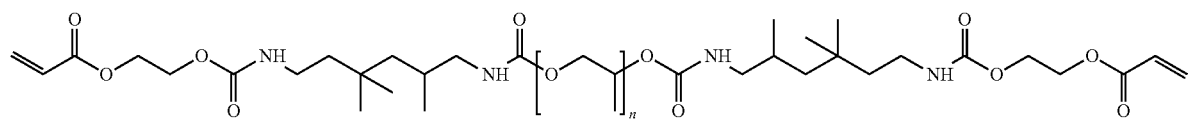

wherein n is 5 to 70, 5 to 60, 5 to 50, 5 to 40, 5 to 30, 5 to 20, or 15 to 20.

A still further suitable polypropylene oxide component is of Formula XII:

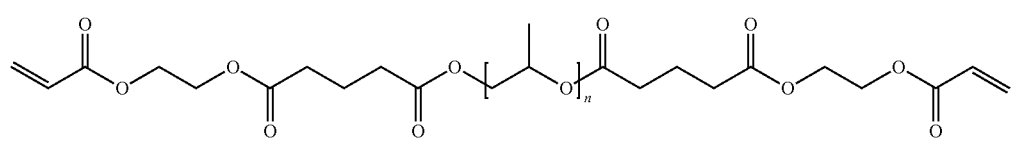

wherein n is 5 to 70, 5 to 60, 5 to 50, 5 to 40, 5 to 30, 5 to 20, or 15 to 20.

Synthesis of the polypropylene oxide components of Formulas VII to XII are described in detail in the Examples below. PPO multimethacrylates are made following a variety of synthetic protocols, some of which are shown in the Examples section below. For example, PPO diols are converted into PPO di- or tetramethacrylate by reacting them with methacrylic acid, methacrylated carboxylic acids such as succinic acid (or glutaric acid) mono-HEMA, and methacrylic acid anhydride. PPO urethane methacrylates are prepared either by reacting PPO diols with isocyanate-carrying methacrylates such as IEM (2-isocyanatoethyl methacrylate), or by reacting the diols with a 2 equivalent di-isocyanate linker such as isophorone diisocyanate (IPDI) or trimethylhexamethylene diisocyanate (TMHDI), followed by capping the unreacted isocyanates with a hydroxyl-carrying methacrylate such as HEMA, HEA, or any hydroxyalkyl methacrylate.

The (e.g., one or more) polypropylene oxide component is present in the photopolymerizable composition in an amount of 1 to 80 wt. %, inclusive, based on the total weight of the photopolymerizable composition, such as 50 to 70 wt. %, inclusive, 10 to 50 wt. %, inclusive, or 10 to 20 wt. %, inclusive. Typically, the polypropylene oxide component is included in the photopolymerizable composition in an amount of 1 wt. % or more, 2 wt. % or more, 5 wt. % or more, 10 wt. % or more, 12 wt. % or more, 15 wt. % or more, 20 wt. % or more, 25 wt. % or more, 30 wt. % or more, or 35 wt. % or more; and 80 wt. % or less, 75 wt. % or less, 70 wt. % or less, 65 wt. % or less, 60 wt. % or less, 55 wt. % or less, 50 wt. % or less, 45 wt. % or less, or 40 wt. % or less, based on the total weight of the photopolymerizable composition.

Urethane Component

The photopolymerizable compositions of the present disclosure optionally include at least one urethane component. As used herein, a "urethane component" refers to a compound including one or more carbamate functionalities in the backbone of the compound. In certain embodiments, the carbamate functionality is of Formula B:

—N(H)—C(O)O—  B.

Urethanes are prepared by the reaction of an isocyanate with an alcohol to form carbamate linkages. Moreover, the term "polyurethane" has been used more generically to refer to the reaction products of polyisocyanates with any polyactive hydrogen compound including polyfunctional alcohols, amines, and mercaptans.

The (e.g., optionally at least one) urethane component typically provides both toughness (e.g., at least a minimum tensile strength and/or modulus) and flexibility (e.g., at least a minimum elongation at break) to the final article. In some embodiments, in addition to the urethane functionality, the urethane component further comprises one or more functional groups selected from hydroxyl groups, carboxyl groups, amino groups, and siloxane groups. These functional groups can be reactive with other components of the photopolymerizable composition during polymerization. The optional urethane component often comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof. The linking group is a functional group that connects two or more urethane groups, and may be divalent, trivalent, or tetravalent. In select embodiments, the at least one urethane component comprises a urethane (meth)acrylate comprising a polyalkylene oxide linking group, a polyamide linking group, or combinations thereof.

For example, the polymerizable component can include polyfunctional urethane acrylates or urethane methacrylates. These urethane (meth)acrylates are known to the person skilled in the art and can be prepared in a known manner by, for example, reacting a hydroxyl-terminated polyurethane with acrylic acid, methacrylic acid, or isocyanatoethyl methacrylate, or by reacting an isocyanate-terminated prepolymer with hydroxyalkyl (meth)acrylates to give the urethane (meth)acrylate. Suitable processes are disclosed, inter alia, in U.S. Pat. No. 8,329,776 (Hecht et al.) and U.S. Pat. No. 9,295,617 (Cub et al.). Suitable urethane methacrylates can include PEGDMA (polyethyleneglycol dimethacrylate having a molecular weight of approximately 400), aliphatic urethane methacrylates, aliphatic polyester urethane methacrylates, and aliphatic polyester triurethane acrylates.

Typically, the urethane component comprises a number average molecular weight (Mn) of 200 grams per mole to 5,000 grams per mole. The number average molecular weight may be measured by matrix assisted laser deposition ionization mass spectrometry (MALDI). The "urethane component" as used herein optionally includes each of a "high Mn urethane component" and a "low Mn urethane component". The high Mn urethane component encompasses compounds including one or more urethane functionalities in the backbone of the compound and that have a number average molecular weight of 1,000 grams per mole (g/mol) or greater, with the proviso that all branches off the backbone of the compound, if present, have a Mn of no more than 200 g/mol. Stated another way, the high Mn urethane component typically has a Mn of 1,000 g/mol or greater, 1,100 g/mol or greater, 1,200 g/mol or greater, 1,300 g/mol or greater, 1,400 g/mol or greater, 1,500 g/mol or greater, 1,600 g/mol or greater, 1,700 g/mol or greater, 1,800 g/mol or greater, 2,000 g/mol or greater, 2,250 g/mol or greater, 2,500 g/mol or greater, 2,750 g/mol or greater, 3,000 g/mol or greater, 3,250 g/mol or greater, 3,500 g/mol or greater, 3,750 g/mol or greater, or even 4,000 g/mol or greater; and 5,000 g/mol or less, 4,800 g/mol or less, 4,600 g/mol or less, 4,400 g/mol or less, 4,100 g/mol or less, 3,900 g/mol or less, 3,700 g/mol or less, 3,400 g/mol or less, 3,100 g/mol or less, 2,900 g/mol or less, 2,700 g/mol or less, 2,400 g/mol or less, or 2,200 g/mol or less, or even 1,900 g/mol or less.

The low Mn urethane component encompasses compounds including one or more urethane functionalities in the backbone of the compound and that have either 1) a number average molecular weight of 100 g/mol or greater and up to but not including 1,000 g/mol, or 2) a number average molecular weight of 100 g/mol or greater and 2,000 g/mol or less, with the proviso that a number average molecular weight of any one or more linear portions between two reactive groups and/or branches is up to but not including 1,000 g/mol. For instance, a branched urethane component can have a total Mn of greater than 1,000 g/mol but still be a low Mn urethane component due to having a linear segment between two branching points with a Mn of less than 1,000 g/mol. Stated another way, the 1) category of low Mn urethane components typically have a Mn of 100 g/mol or greater, 150 g/mol or greater, 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and up to but not including 1,000 g/mol, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. The 2) category of low Mn urethane components typically have a Mn of 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and 1,500 g/mol or less, 1,400 g/mol or less, 1,300 g/mol or less, 1,200 g/mol or less, 1,100 g/mol or less, 1,000 g/mol or less, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. Each of the foregoing second category of low Mn urethane components includes the proviso that a number average molecular weight of any one or more linear portions between two reactive groups and/or branches is up to but not including 1,000 g/mol, 950 g/mol or less, 900 g/mol or less, 850 g/mol or less, 800 g/mol or less, or 750 g/mol or less; and a number average molecular weight of any one or more linear portions between two reactive groups and/or branches is 100 g/mol or greater, 200 g/mol or greater, 250 g/mol or greater, 300 g/mol or greater, 350 g/mol or greater, 400 g/mol or greater, 450 g/mol or greater, or 500 g/mol or greater.

The use of high Mn urethane components having a number average molecular weight of 1,000 g/mol or greater tend to provide a final article having at least a certain desirable minimum elongation at break (e.g., 30% or greater). Typically, eighty percent by weight or greater of the (optional) at least one urethane component is provided by one or more high Mn (e.g., long chain) urethane components. More particularly, in embodiment where a low molecular weight urethane component is present, typical ratios of the high number average molecular weight urethane component to the low number average molecular weight urethane component range from 95:5 high Mn urethane component to low Mn urethane component to 80:20 high Mn urethane component to low Mn urethane component. Stated another way, photopolymerizable compositions according to at least certain aspects of the disclosure can include 80 wt. % or more of the total urethane component as a high Mn urethane component, 85 wt. % or more, 87 wt. % or more, 90 wt. % or more, 92 wt. % or more, 95 wt. % or more, or even 97 wt. % or more of the total urethane component as a high Mn urethane component; and 100% or less of the total urethane component as a high Mn urethane component, 98 wt. % or less, 96 wt. % or less, 94 wt. % or less, 91 wt. % or less, 89 wt. % or less, or 86 wt. % or less of the total urethane component as a high Mn urethane component. Similarly, photopolymerizable compositions according to at least certain aspects of the disclosure can include 2 wt. % or more of the total urethane component as a low Mn urethane component, 4 wt. % or more, 5 wt. % or more, 8 wt. % or more, 10 wt. % or more, 12 wt. % or more, 15 wt. % or more, or even 17 wt. % or more of the total urethane component as a low Mn urethane component; and 20 wt. % or less of the total urethane component as a low Mn urethane component, 18 wt. % or less, 16 wt. % or less, 14 wt. % or less, 11 wt. % or less, 9 wt. % or less, 7 wt. % or less, 6 wt. % or less, or 3 wt. % or less of the total urethane component as a low Mn urethane component.

According to certain embodiments, at least one (optional) urethane component comprises at least one (meth)acrylate component having a urethane moiety, which may help to improve physical properties of the cured composition like flexural strength and/or elongation at break. Such a urethane component can be characterized by the following features alone or in combination:

a) comprising at least 2 or 3 or 4 (meth)acrylate moieties;
b) number average molecular weight (Mn): from 1,000 to 5,000 g/mol or from 1,000 to 2000 g/mol;
c) comprising a C1 to C20 linear or branched alkyl moiety to which the (meth)acrylate moieties are attached through urethane moieties;
d) viscosity: from 1=0.1 to 100 Pa·s or 1 to 50 Pa·s at 23° C.

A combination of the features a) and b) or b) and c) or a) and d) can sometimes be preferred.

Urethane (meth)acrylates may be obtained by a number of processes known to the skilled person. The urethane(meth) acrylates are typically obtained by reacting an NCO-terminated compound with a suitable monofunctional (meth) acrylate monomer such as hydroxyethyl acrylate, hydroxyethyl methacrylate, hydroxypropylmethacrylate, preferably hydroxyethyl- and hydroxypropylmethacrylate. For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates. Any of the known polyisocyanates such as alkyl and alkylene polyisocyanates, cycloalkyl and cycloalkylene polyisocyanates, and combinations such as alkylene and cycloalkylene polyisocyanates can be employed. Preferably, diisocyanates having the formula $X(NCO)_2$ can be used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an aliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'-methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetra¬methylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred. Examples of suitable capping agents include 2-hydroxyethyl(meth)acrylate, 2-hydroxypropyl (meth)acrylate, glycerol di(meth)acrylate and/ or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

According to select embodiments containing a urethane component, the urethane dimethacrylate of the following Formulas XIII and XIV are preferred:

XIII

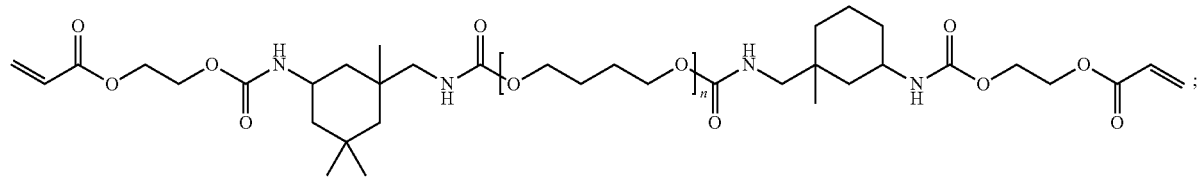

wherein n=9 or 10;

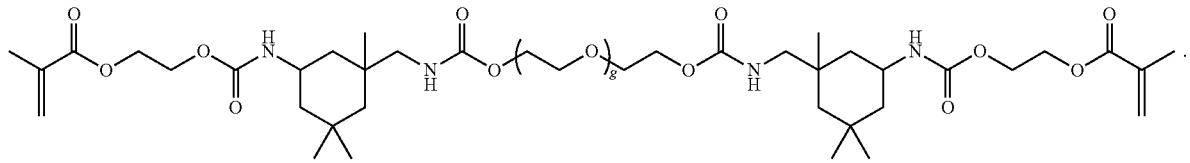

Examples of commercially available urethane components include those available under the trade designations of EXOTHANE 108 (e.g., Formula I), EXOTHANE 8, and EXOTHANE 10 (e.g., Formula II) from Esstech Inc, and DESMA from 3M Company. DESMA is described in, e.g., paragraph [0135] and Table 3 of EP2167013B1 (Hecht et al.).

In certain embodiments, a urethane component (e.g., an oligomer or a polymer) may be prepared including one or more pendant groups attached to the urethane backbone. Preferably, at least one pendent group comprises a photoinitiator. For instance, a photoinitiator-containing ethyl acrylate compound (PIEA) has been prepared via the below reaction scheme:

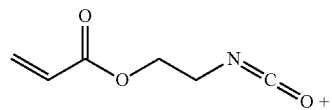

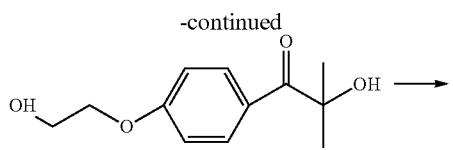

-continued

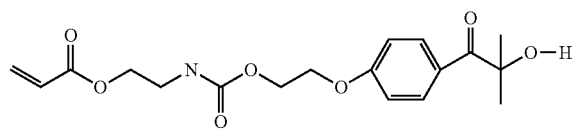

The reaction is described in detail in co-owned Application Ser. No. 62/589,707. Next, the PIEA can be reacted with one or more monomers and a thermal initiator in solution, such as per the below reaction scheme:

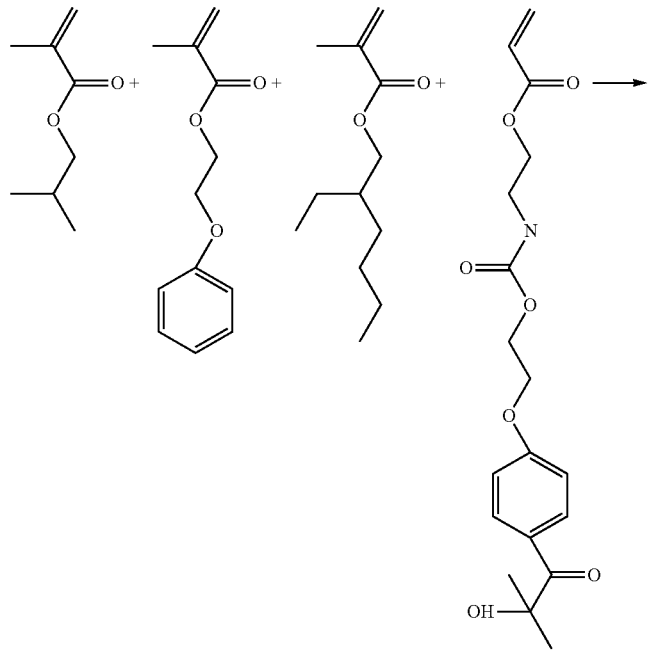

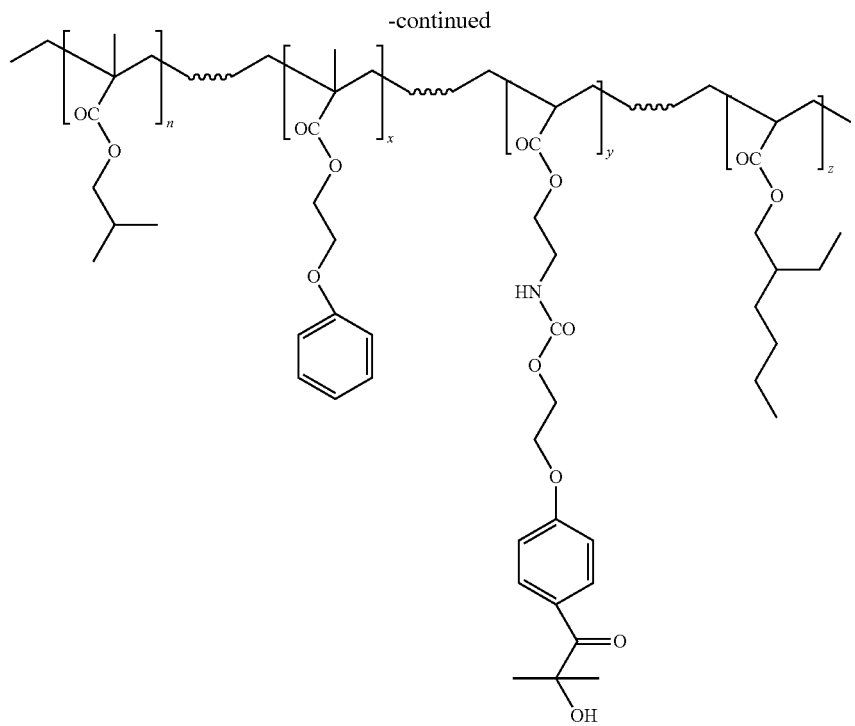

This reaction is also described in detail in co-owned Application Ser. No. 62/589,707. Such photoinitiator-carrying urethane components may be included in photopolymerizable compositions of at least certain embodiments of the present disclosure. An advantage to providing the photoinitiator attached to the urethane component is that the location of polymerization at the urethane backbone can be preselected.

The urethane component, when present, is often included in the photopolymerizable composition in an amount of 30 to 90 wt. %, inclusive, based on the total weight of the photopolymerizable composition, such as 50 to 90 wt. %, inclusive, or 60 to 80 wt. %, inclusive. Typically, the urethane component is included in the photopolymerizable composition in an amount of 30 wt. % or more, 35 wt. % or more, 40 wt. % or more, 45 wt. % or more, 50 wt. % or more, 65 wt. % or more, 60 wt. % or more, 65 wt. % or more, 70 wt. % or more, or 75 wt. % or more; and 90 wt. % or less, 87 wt. % or less, 85 wt. % or less, 80 wt. % or less, or 77 wt. % or less, based on the total weight of the photopolymerizable composition.

Reactive Diluent

The photopolymerizable compositions of the present disclosure optionally include at least one reactive diluent. A "reactive diluent," for reference purposes herein, is a component that contains at least one free radically reactive group (e.g., an ethylenically-unsaturated group) that can co-react with the at least one polypropylene oxide component (e.g., is capable of undergoing addition polymerization). The reactive diluent has a smaller molecular weight than at least one polypropylene oxide component, often less than 400 grams per mole, and does not contain any urethane functional groups (e.g., is free of any urethane functional groups).

In select embodiments, the (optional) reactive diluent comprises a (meth)acrylate, a polyalkylene oxide di(meth) acrylate, an alkane diol di(meth)acrylate, or combinations thereof, such as a (meth)acrylate.

Suitable free-radically polymerizable reactant diluents include di-, tri-, or other poly-acrylates and methacrylates such as glycerol diacrylate, ethoxylated bisphenol A dimethacrylate (D-zethacrylate), tetraethylene glycol dimethacrylate (TEGDMA), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyl-dimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); polyfunctional (meth)acrylates comprising urea or amide groups, such as those of EP2008636 (Hecht et al.).

The (optional) reactive diluent can comprise one or more poly(meth)acrylates, for example, di-, tri-, tetra- or pentafunctional monomeric or oligomeric aliphatic, cycloaliphatic or aromatic acrylates or methacrylates.

Examples of suitable aliphatic poly(meth)acrylates having more than two (meth)acrylate groups in their molecules are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate.

Another suitable class of free radical polymerizable compounds includes aromatic di(meth)acrylate compounds and trifunctional or higher functionality (meth)acrylate compound. Trifunctional or higher functionality meth(acrylates) can be tri-, tetra- or pentafunctional monomeric or oligomeric aliphatic, cycloaliphatic or aromatic acrylates or methacrylates.

Examples of suitable aliphatic tri-, tetra- and pentafunctional (meth)acrylates are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate. Further examples of suitable aromatic tri(meth)acrylates are the reaction products of triglycidyl ethers of trihydroxy benzene and phenol or cresol novolaks containing three hydroxyl groups, with (meth)acrylic acid.

In some cases, a reactive diluent comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis(4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. In certain embodiments, the (optional) reactive diluent comprises a polyester methacrylate, which is a methacrylate including two or more ester groups. Suitable commercially available polyester methacrylates include for instance triethyleneglycol dimethacrylate (TEGDMA) from Sigma-Aldrich (St. Louis, MO) and 1,12-dodecanediol dimethacrylate (DDDMA) from Esstech, Inc (Essington, PA). In some cases, a reactive diluent described herein comprises one or more higher functional acrylates or methacrylates such as dipentaerythritol monohydroxy pentaacrylate or bis(trimethylolpropane)tetraacrylate.

Suitable free-radically polymerizable monofunctional reactive diluents include phenoxy ethyl(meth)acrylate, phenoxy-2-methylethyl(meth)acrylate, phenoxyethoxyethyl (meth)acrylate, 3-hydroxy-2-hydroxypropyl(meth)acrylate, benzyl(meth)acrylate, phenylthio ethyl acrylate, 2-naphthylthio ethyl acrylate, 1-naphthylthio ethyl acrylate, 2,4,6-tribromophenoxy ethyl acrylate, 2,4-dibromophenoxy ethyl acrylate, 2-bromophenoxy ethyl acrylate, 1-naphthyloxy ethyl acrylate, 2-naphthyloxy ethyl acrylate, phenoxy 2-methylethyl acrylate, phenoxyethoxyethyl acrylate, 3-phenoxy-2-hydroxy propyl acrylate, 2,4-dibromo-6-sec-butylphenyl acrylate, 2,4-dibromo-6-isopropylphenyl (meth)acrylate, benzyl (meth)acrylate, phenyl (meth)acrylate, tetrahydrofurfuryl (meth)acrylate, alkoxylated tetrahydrofurfuryl acrylate, ethoxylated nonyl phenol (meth)acrylate, alkoxylated lauryl (meth)acrylate, alkoxylated phenol (meth)acrylate, stearyl (meth)acrylate, tetrahydrofurfuryl (meth)acrylate, lauryl (meth)acrylate, isodecyl (meth)acrylate, isooctyl (meth)acrylate, octadecyl (meth)acrylate, tridecyl (meth)acrylate, ethoxylated (4) nonyl phenol (meth) acrylate, caprolactone (meth)acrylate, cyclic trimethylolpropane formal (meth)acrylate, 3,3,5-trimethylcyclohexyl (meth)acrylate, dicyclopentadienyl (meth)acrylate, isobutyl (meth)acrylate, n-butyl (meth)acrylate, ethyl hexyl (meth)acrylate, isobornyl (meth)acrylate, and 2,4,6-tribromophenyl (meth)acrylate.

In certain embodiments, the photopolymerizable composition consists essentially of multifunctional components or is free of monofunctional components. This means that the photopolymerizable composition contains 2 wt. % or less of monofunctional components. An advantage of such photopolymerizable compositions is that they tend to contain a minimal to zero amount of unreacted reactive diluent that is capable of leaching out of an article following cure. For applications in which the article is an orthodontic article, this minimizes release of unreacted reactive diluent into a patient's mouth.

In certain embodiments, the (optional) reactive diluent has a molecular weight of 400 grams per mole or less, 375 g/mol or less, 350 g/mol or less, 325 g/mol or less, 300 g/mol or less, 275 g/mol or less, 225 g/mol or less, or 200 g/mol or less. Including one or more reactive diluents with such molecular weights can assist in providing a photopolymerizable composition that has a sufficiently low viscosity for use with vat polymerization methods. In certain embodiments, the at least one reactive diluent comprises a molecular weight of 200 g/mol to 400 g/mol, inclusive.

The reactive diluent, when present, is included in the photopolymerizable composition in an amount of 1 to 30 wt. %, inclusive, based on the total weight of the photopolymerizable composition, such as 5 to 25 wt. %, inclusive. The reactive diluent can be included in the photopolymerizable composition in an amount of 1 wt. % or more, 3 wt. % or more, 5 wt. % or more, 10 wt. % or more, 12 wt. % or more, or 15 wt. % or more; and 30 wt. % or less, 27 wt. % or less, 25 wt. % or less, 22 wt. % or less, 20 wt. % or less, or 18 wt. % or less, based on the total weight of the photopolymerizable composition.

Additives

Photopolymerizable compositions described herein, in some instances, further comprise one or more additives, such as one or more additives selected from the group consisting of photoinitiators, inhibitors, stabilizing agents, sensitizers, absorption modifiers, fillers and combinations thereof. For example, the photopolymerizable composition further comprises one or more photoinitiators. Suitable exemplary photoinitiators are those available under the trade designations IRGACURE and DAROCUR from BASF (Ludwigshafen, Germany) and include 1-hydroxycyclohexyl phenyl ketone (IRGACURE 184), 2,2-dimethoxy-1, 2-diphenylethan-1-one (IRGACURE 651), bis(2,4,6 trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), Oligo[2-hydroxy-2-methyl-1-[4-(1-methylvinyl)phenyl]propanone] ESACURE ONE (Lamberti S.p.A., Gallarate, Italy), 2-hydroxy-2-methyl-1-phenyl propan-1-one (DAROCUR 1173), 2, 4, 6-trimethylbenzoyldiphenylphosphine oxide (IRGACURE TPO), and 2,4,6-trimethylbenzoylphenyl phosphinate (IRGACURE TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

A photoinitiator can be present in a photopolymerizable composition described herein in any amount according to the particular constraints of the additive manufacturing process. In some embodiments, a photoinitiator is present in a photopolymerizable composition in an amount of up to about 5% by weight, based on the total weight of the photopolymerizable composition. In some cases, a photoinitiator is present in an amount of about 0.1-5% by weight, based on the total weight of the photopolymerizable composition.

A thermal initiator can be present in a photopolymerizable composition described herein in any amount according to the particular constraints of the additive manufacturing process. In some embodiments, a thermal initiator is present in a photopolymerizable composition in an amount of up to about 5% by weight, based on the total weight of the photopolymerizable composition. In some cases, a thermal initiator is present in an amount of about 0.1-5% by weight, based on the total weight of the photopolymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2-azo-bis(isobutyronitrile), and t-butyl perbenzoate. Examples of commercially available thermal initiators include initiators available from DuPont Specialty Chemical (Wilmington, DE) under the VAZO trade designation including VAZO 67 (2,2'-azo-bis(2-methybutyronitrile)) VAZO 64 (2,2'-azo-bis(isobutyronitrile)) and VAZO 52 (2,2'-azo-bis(2,2-dimethyvaleronitrile)), and LUCIDOL 70 from Elf Atochem North America, Philadelphia, PA.

In certain aspects, the use of more than one initiator assists in increasing the percentage of reactive diluent that gets incorporated into the reaction product and thus decreasing the percentage of the reactive diluent that remains uncured.

In addition, a photopolymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the photopolymerizable composition, a sensitizer can be present in an amount ranging of about 0.01% by weight or about 1% by weight, based on the total weight of the photopolymerizable composition.

A photopolymerizable composition described herein optionally also comprises one or more polymerization inhibitors or stabilizing agents. A polymerization inhibitor is often included in a photopolymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the photopolymerizable composition. Further, if used, a stabilizing agent is present in a photopolymerizable composition described herein in an amount of about 0.1-5% by weight, about 0.5-4% by weight, or about 1-3% by weight, based on the total weight of the photopolymerizable composition.

A photopolymerizable composition as described herein can also comprise one or more absorption modifiers (e.g., dyes, optical brighteners, pigments, particulate fillers, etc.) to control the penetration depth of actinic radiation. One particularly suitable absorption modifier is Tinopal OB, a benzoxazole, 2,2'-(2,5-thiophenediyl)bis[5-(1,1-dimethylethyl)], available from BASF Corporation, Florham Park, NJ The absorption modifier, if used, can be present in an amount of about 0.001-5% by weight, about 0.01-1% by weight, about 0.1-3% by weight, or about 0.1-1% by weight, based on the total weight of the photopolymerizable composition.

Photopolymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, OH and CAB-O-SIL M5 and TS-720 silica from Cabot Corp., Tuscola, IL). Organic fillers made from polymeric materials are also possible, such as those disclosed in International Publication No. WO09/045752 (Kalgutkar et al.).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, MN). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at OX magnification.

Suitable fibers include for instance ceramic fibers available under the trade name NEXTEL (available from 3M Company, St. Paul, MN), such as NEXTEL 312, 440, 610 and 720. One presently preferred ceramic fiber comprises polycrystalline $\alpha$-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, MN). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, MN). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the photopolymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Photopolymerizable compositions materials herein can also exhibit a variety of desirable properties, non-cured, cured, and as post-cured articles. A photopolymerizable composition, when non-cured, has a viscosity profile consistent with the requirements and parameters of one or more additive manufacturing devices (e.g., 3D printing systems). In some instances, a photopolymerizable composition described herein when non-cured exhibits a dynamic viscosity of about 0.1-1,000 Pa·s, about 0.1-100 Pa·s, or about 1-10 Pa·s using a TA Instruments AR-G2 magnetic bearing rheometer using a 40 mm cone and plate measuring system at 40 degrees Celsius and at a shear rate of 0.1 l/s, when measured according to ASTM D4287, as set forth in the Example Test Method below. In some cases, a photopolymerizable composition described herein when non-cured exhibits a dynamic viscosity of less than about 10 Pa·s, when measured according to modified ASTM D4287.

Articles and Methods

In a second aspect, the present disclosure provides an article. The article comprises a reaction product of a photopolymerizable composition, the photopolymerizable composition comprising a blend of:
   a. 1 to 80 wt. %, inclusive, of at least one polypropylene oxide component based on the total weight of the photopolymerizable composition, the polypropylene oxide component comprising i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof,
   b. optionally 30 wt. % or greater of at least one urethane component, if present, based on the total weight of the photopolymerizable composition; with the proviso that when the at least one urethane component is not present the at least one polypropylene oxide component comprises at least two functional groups selected from oxycarbonylamino, amino carbonyloxy, and combinations thereof,
   c. optionally at least one multifunctional reactive diluent in an amount of 1 to 30 wt. %, inclusive, if present, based on the total weight of the photopolymerizable composition;
   d. 0.1 to 5 wt. %, inclusive, of at least one initiator; and
   e. an optional inhibitor in an amount of 0.001 to 1 wt. %, inclusive, if present, based on the total weight of the photopolymerizable composition.

The components (a) through (e) are as discussed in detail above. In many embodiments, the photopolymerizable composition of the article is vat polymerized, as discussed in detail below. Optionally, when formed using additive manufacturing methods, the article comprises a plurality of layers.

The shape of the article is not limited, and may comprise a film or a shaped integral article. For instance, a film may readily be prepared by casting the photopolymerizable composition according to the first aspect, then subjecting the cast composition to actinic radiation to polymerize the photopolymerizable composition. In many embodiments, the article comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods. In select embodiments, the article comprises an orthodontic article. Orthodontic articles are described in further detail below.

In a third aspect, the present disclosure provides a method of making an article. The method comprises:
   a. providing a photopolymerizable composition, the photopolymerizable composition comprising a blend of:
      i. 1 to 80 wt. %, inclusive, of at least one polypropylene oxide component based on the total weight of the photopolymerizable composition, the polypropylene oxide component comprising i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof,
      ii. optionally 30 wt. % or greater of at least one urethane component, if present, based on the total weight of the photopolymerizable composition; with the proviso that when the at least one urethane component is not present the at least one polypropylene oxide component comprises at least two functional groups selected from oxycarbonylamino, amino carbonyloxy, and combinations thereof,
      iii. optionally at least one multifunctional reactive diluent in an amount of 1 to 30 wt. %, inclusive, if present, based on the total weight of the photopolymerizable composition;
      iv. 0.1 to 5 wt. %, inclusive, of at least one initiator; and
      v. an optional inhibitor in an amount of 0.001 to 1 wt. %, inclusive, if present, based on the total weight of the photopolymerizable composition; and
   b. selectively curing the photopolymerizable composition to form an article;
   c. optionally curing unpolymerized polypropylene oxide component, urethane component, and/or reactive diluent remaining after step (b).

The components (a) through (e) are as discussed in detail above. In many embodiments, the photopolymerizable composition is cured using actinic radiation comprising UV radiation, e-beam radiation, visible radiation, or a combination thereof. Moreover, the method optionally further comprises post curing the article using actinic radiation or heat.

In additive manufacturing methods, the method further comprises (d) repeating steps (a) and (b) to form multiple layers and create the article comprising a three-dimensional structure prior to step (c). In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall.

A photopolymerizable composition described herein in a cured state, in some embodiments, can exhibit one or more desired properties. A photopolymerizable composition in a "cured" state can comprise a photopolymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured photopolymerizable composition is at least about 50%, at least about 70%, at least about 80%, or at least about 90% polymerized or crosslinked. A cured photopolymerizable composition can also be between about 10% and about 99% polymerized or crosslinked.

The conformability and durability of a cured article made from the photopolymerizable compositions of the present disclosure can be determined in part by standard tensile, modulus, and/or elongation testing. The photopolymerizable compositions can typically be characterized by at least one of the following parameters after hardening. Advantageously, the elongation at break is typically 25% or greater, 27% or greater, 30% or greater, 32% or greater, 35% or greater, 40% or greater, 45% or greater, 50% or greater, 55% or greater, or 60% or greater; and 200% or less, 100% or less, 90% or less, 80% or less, or 70% or less. Stated another way, the elongation at break of the cured article can range from 25% to 200%. In some embodiments, the elongation at break is at least 30% and no greater than 120%. The ultimate tensile strength is typically 10 MegaPascals (MPa) or greater, 15 MPA or greater, 20 MPa or greater, or 25 MPa or greater, and is typically 80 MPa or less, each as determined according to ASTM D638-10. While the urethane component has the greatest effect on the elongation at break of an article, other components of the photopolymerizable composition also impact the elongation at break, e.g., the length of a linear chain or branch of a reactive diluent tends to be positively correlated to the elongation at break of the final article. The tensile modulus is typically 50 MPa or greater, as determined according to ASTM D638-10. Such elongation properties can be measured, for example, by the methods outlined in ASTM D638-10, using test specimen Type V. The mechanical properties above are particularly well suited for articles that require resiliency and flexibility, along with adequate wear strength and low hygroscopicity.

Photopolymerizable compositions described herein can be mixed by known techniques. In some embodiments, for instance, a method for the preparation of a photopolymerizable composition described herein comprises the steps of mixing all or substantially all of the components of the photopolymerizable composition, heating the mixture, and optionally filtering the heated mixture. Softening the mixture, in some embodiments, is carried out at a temperature of about 50° C. or in a range from about 50° C. to about 85° C. In some embodiments, a photopolymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

Fabricating an Article

Once prepared as set forth above, the photopolymerizable compositions of the present disclosure may be used in myriad additive manufacturing processes to create a variety of articles, including casting a film as noted above. A generalized method 100 for creating three-dimensional articles is illustrated in FIG. 1. Each step in the method will be discussed in greater detail below. First, in Step 110 the desired photopolymerizable composition (e.g., comprising at least one polypropylene oxide component) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three-dimensional structure (e.g., an orthodontic aligner). Optionally uncured photopolymerizable composition is removed from the article in Step 140, and further optionally, the article is subjected to additional curing to polymerize remaining uncured photopolymerizable components in the article in Step 150.

Methods of printing a three-dimensional article or object described herein can include forming the article from a plurality of layers of a photopolymerizable composition described herein in a layer-by-layer manner. Further, the layers of a build material composition can be deposited according to an image of the three-dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, SC and the Asiga PICO PLUS 39, available from Asiga USA, Anaheim Hills, CA.

Figure 2:
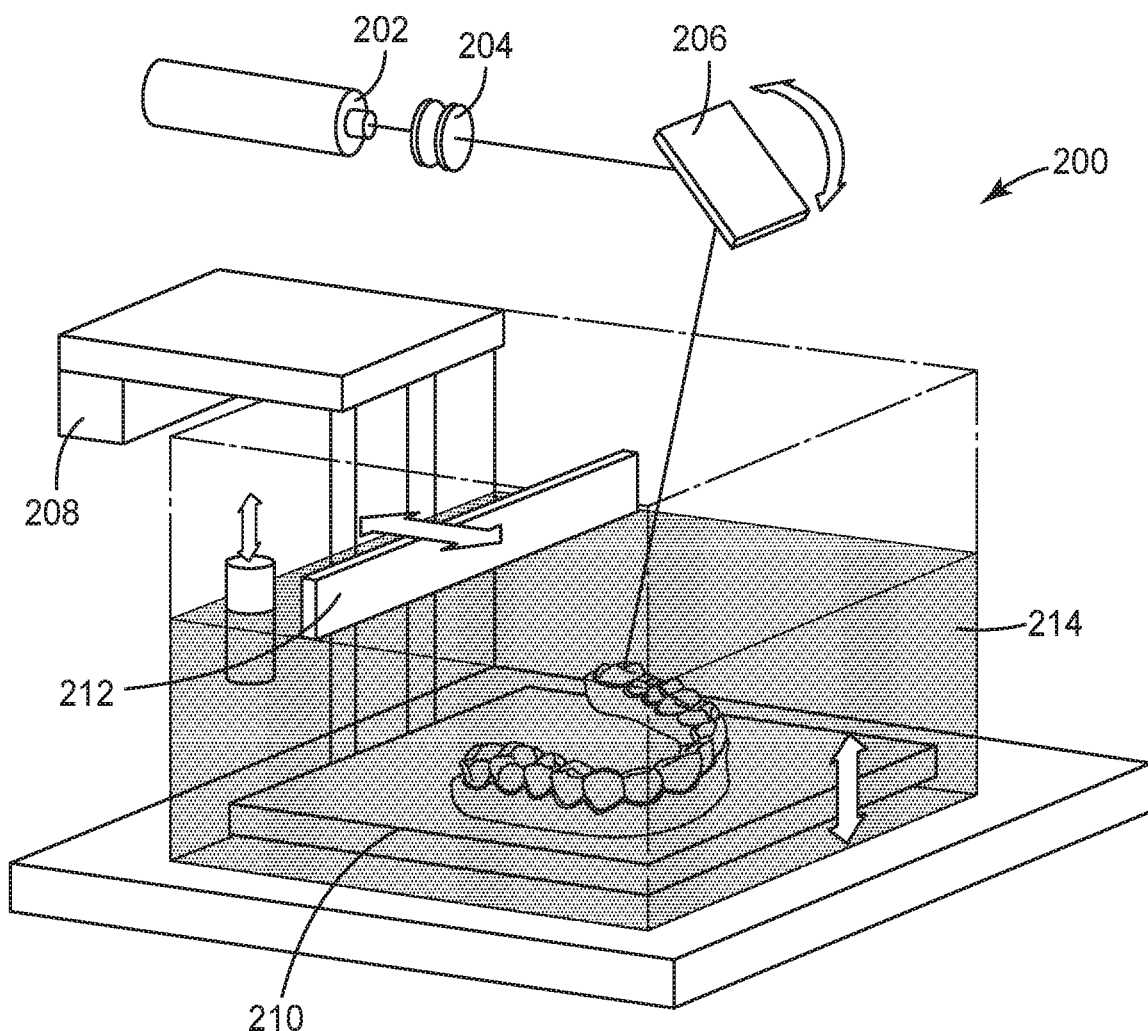
FIG. 2 is a generalized schematic of a stereolithography apparatus.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, CA), for instance as described in U.S. Pat. Nos. 9,205,601 and 9,360,757 (both to DeSimone et al.).

Figure 5:
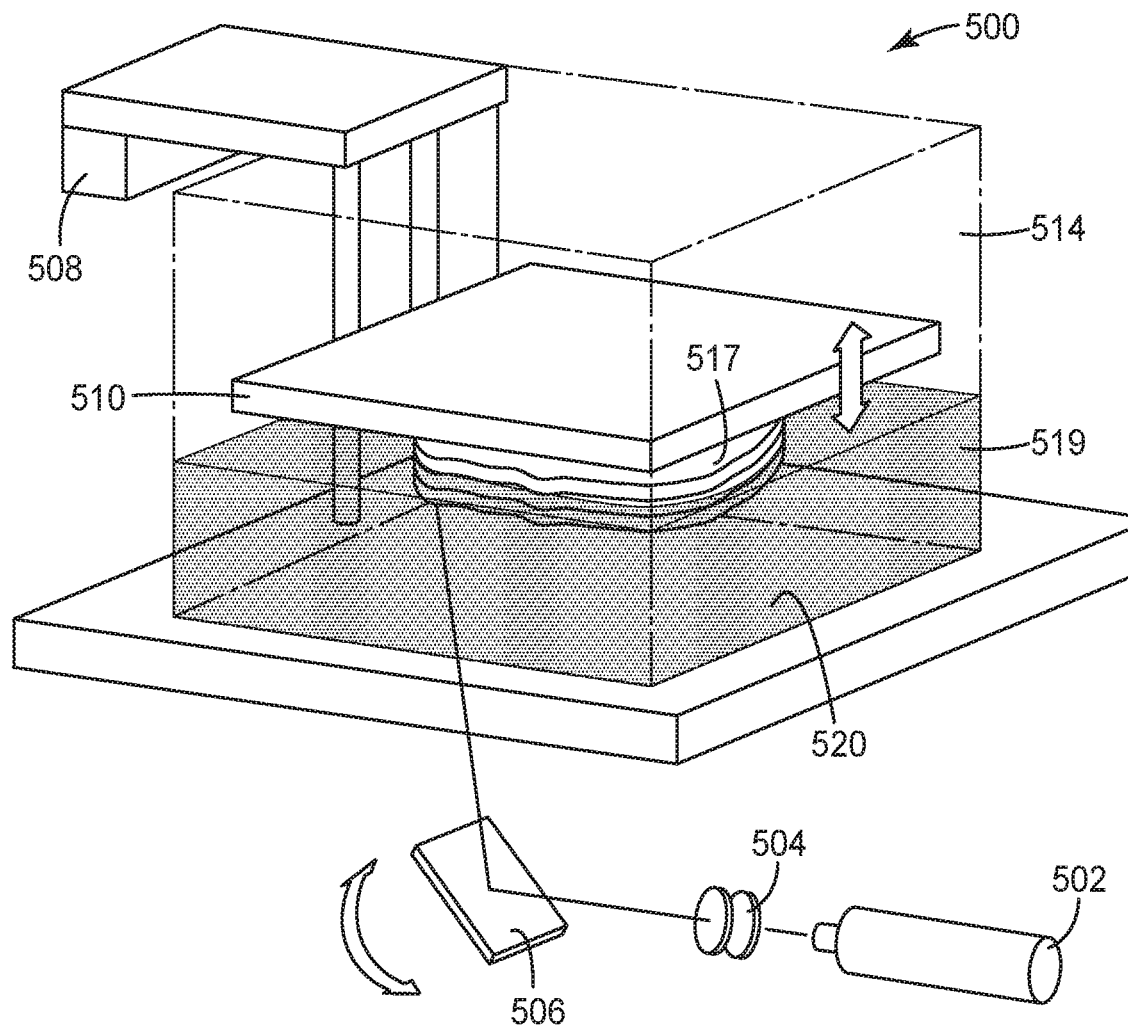
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional post curing. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to post curing.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be post cured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure process of Step 150. In general, post curing improves the mechanical properties and stability of the three-dimensional article relative to the same three-dimensional article that is not post cured.

The following describes general methods for creating a clear tray aligner as printed appliance 300. However, other dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

Alternatively, the photopolymerizable compositions can be used in other industries, such as aerospace, animation and entertainment, architecture and art, automotive, consumer goods and packaging, education, electronics, hearing aids, sporting goods, jewelry, medical, manufacturing, etc.

Fabricating an Orthodontic Appliance with the Photopolymerizable Compositions

Figure 3:
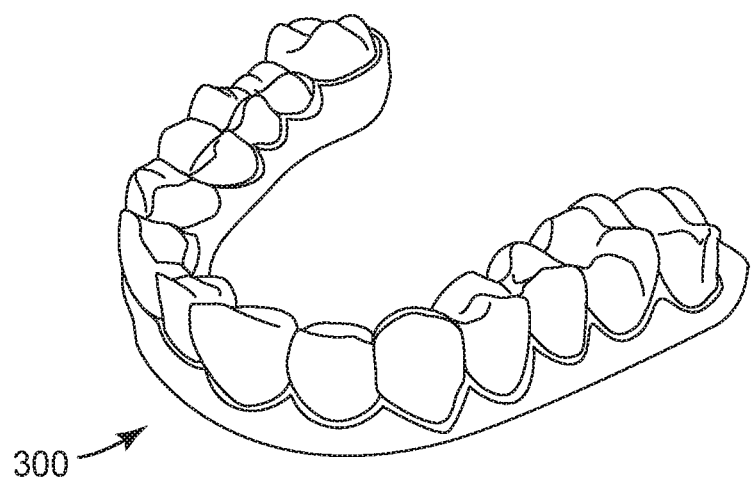
FIG. 3 is an isometric view of a printed clear tray aligner, according to one embodiment of the present disclosure.

One particularly interesting implementation of an article is generally depicted in FIG. 3. The additive manufactured article 300 is a clear tray aligner and is removably positionable over some or all of a patient's teeth. In some embodiments, the appliance 300 is one of a plurality of incremental adjustment appliances. The appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of the receptacles may be aligned to apply rotational and/or translational forces to the corresponding tooth of the patient when the appliance 300 is worn by the patient in order to eventually align said tooth to a new desired position. In some particular examples, the appliance 300 may be configured to provide only compressive or linear forces. In the same or different examples, the appliance 300 may be configured to apply translational forces to one or more of the teeth within receptacles.

In some embodiments, the shell of the appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. An appliance 300 can accordingly be designed such that any receptacle is shaped to facilitate retention of the tooth in a particular position in order to maintain the current position of the tooth.

Figure 4:
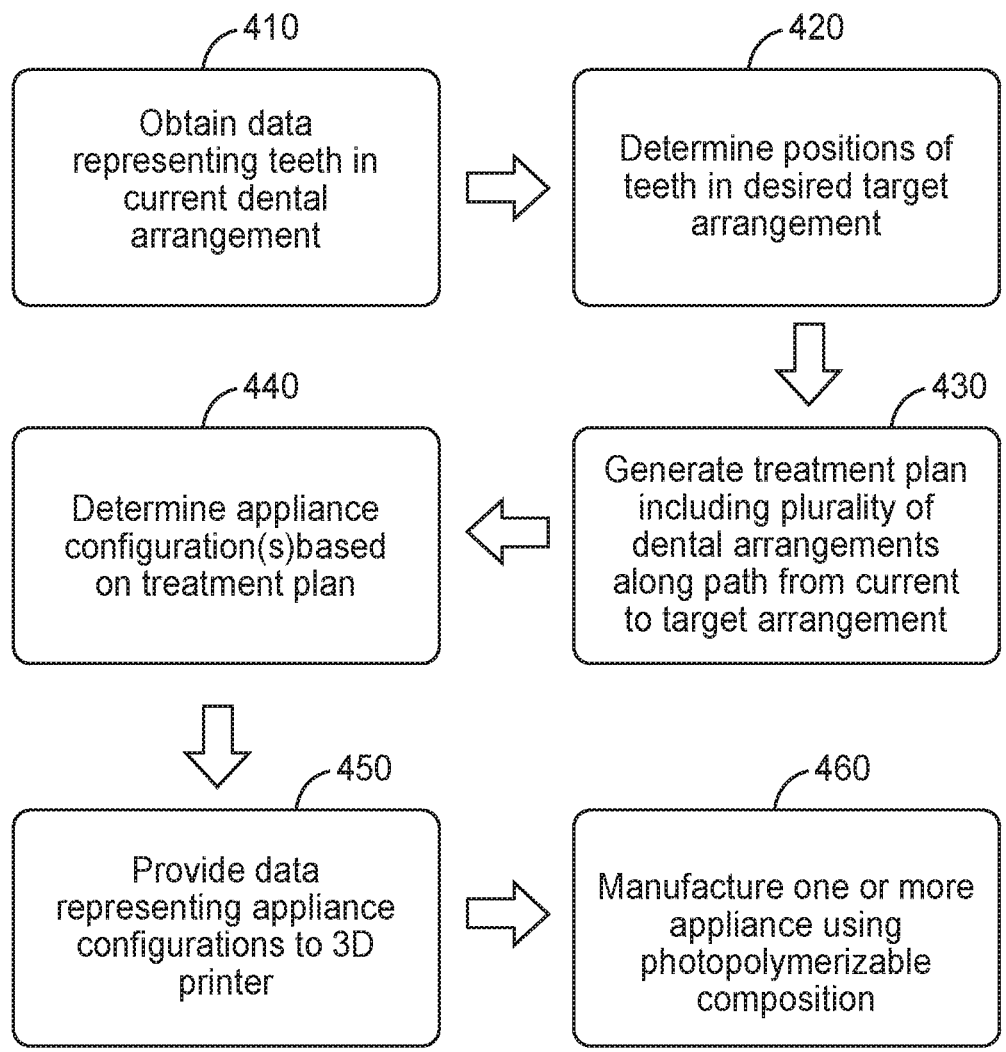
FIG. 4 is a flowchart of a process for manufacturing a printed orthodontic appliance according to the present disclosure.

A method 400 of creating an orthodontic appliance using the photopolymerizable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to an additive manufacturing device (e.g., a 3D printer system) (Step 450). An appliance can be manufactured using a photopolymerizable composition of the present disclosure retained in the additive manufacturing device (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition, the photopolymerizable composition includes a blend of (a) 1 to 80 wt. %, inclusive, of at least one polypropylene oxide component based on the total weight of the photopolymerizable composition, the polypropylene oxide component comprising i) two (meth) acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition. The components (a) through (e) are as discussed in detail above. In certain embodiments, the article is an orthodontic article. Preferably, the article has an elongation at break of 30% or greater.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In embodiments wherein the article is an orthodontic article, scanning techniques may include, for example, scanning a patient's mouth to customize an orthodontic article for the patient.

Figure 10:
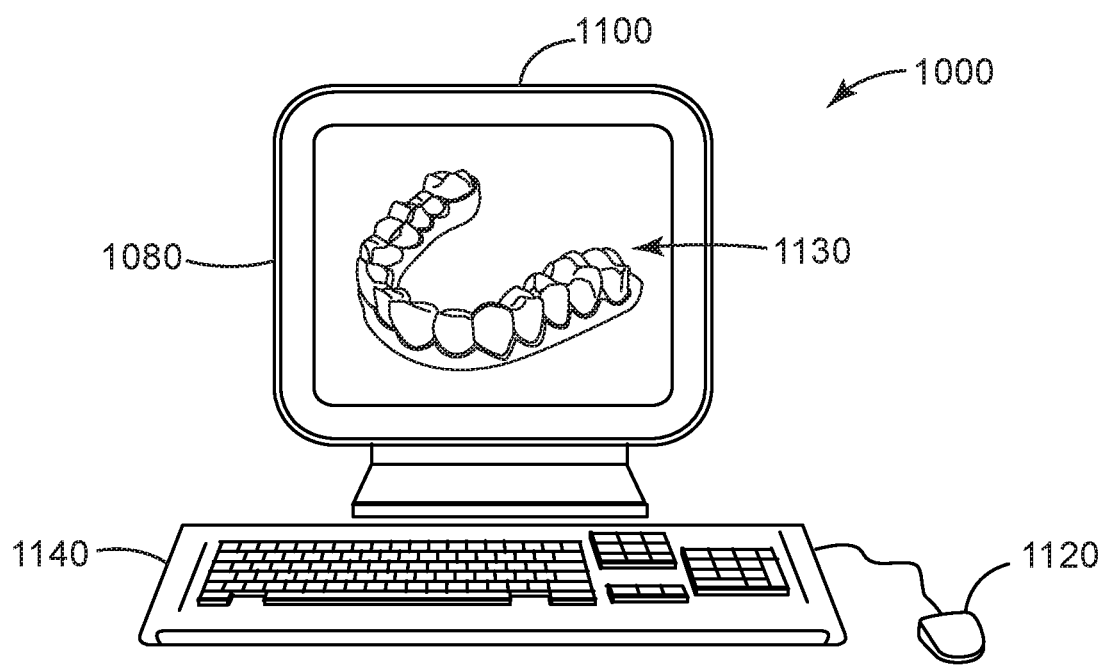
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner 1130 is shown on the display 1100.

Figure 6:
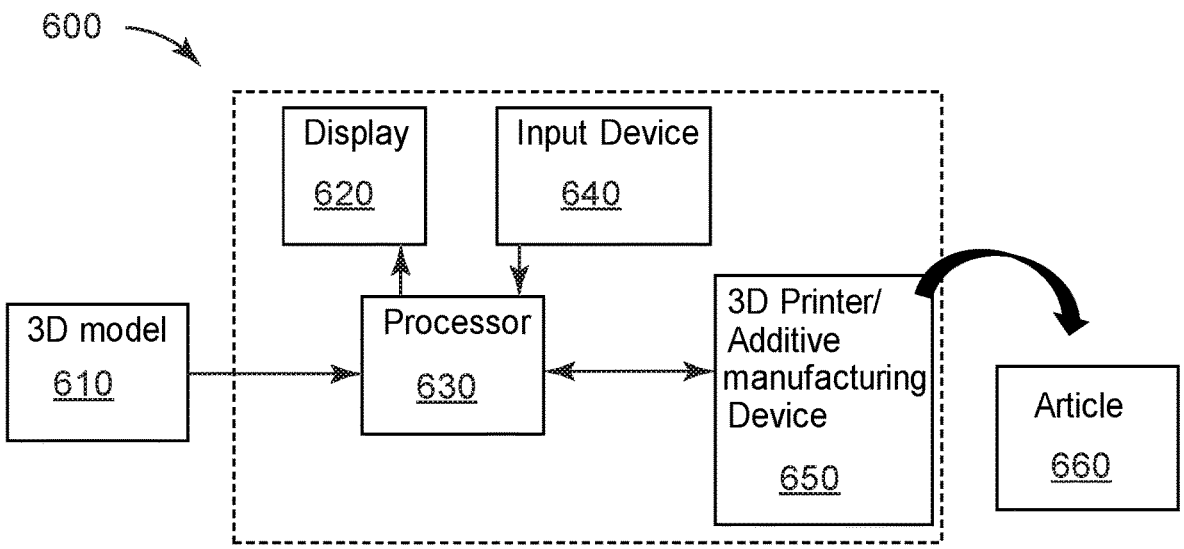
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition, the photopolymerizable composition includes a blend of (a) 1 to 80 wt. %, inclusive, of at least one polypropylene oxide component based on the total weight of the photopolymerizable composition, the polypropylene oxide component comprising i) two (meth) acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition. The components (a) through (e) are as discussed in detail above.

Figure 7:
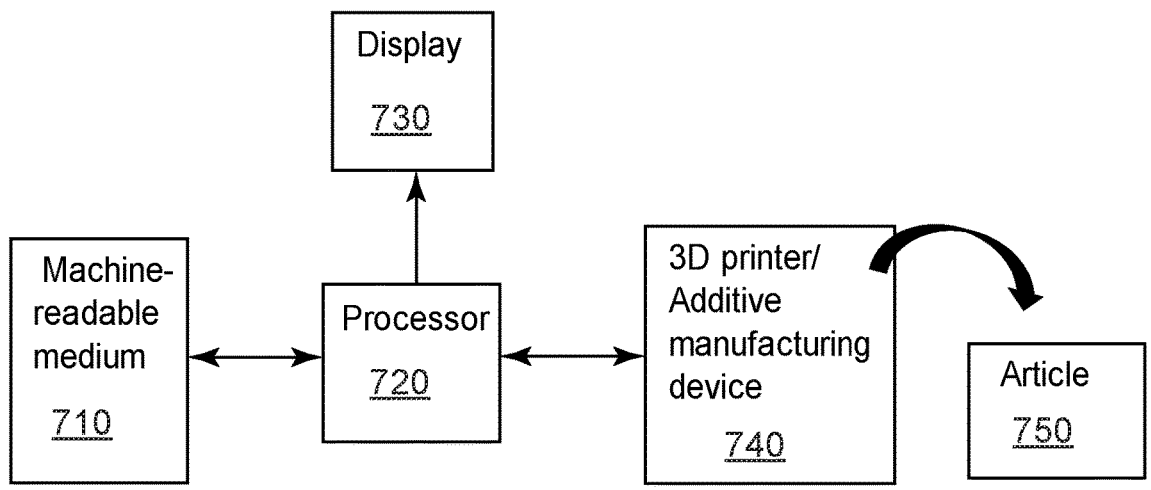
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner 1130 as shown on the display 1100 of FIG. 10) from the machine-readable medium 710.

Figure 8:
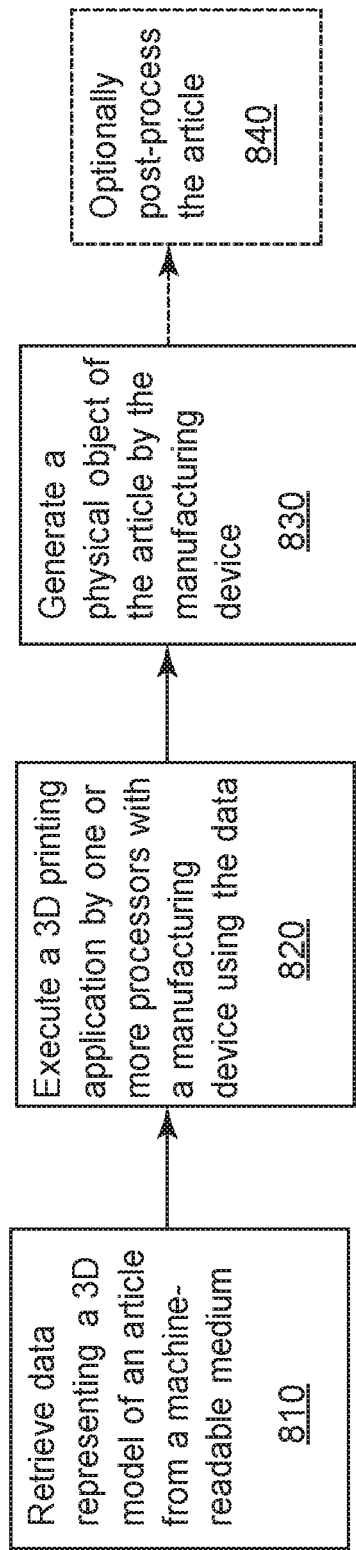
FIG. 8 is a high-level flow chart of an exemplary article manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition, the photopolymerizable composition includes a blend of (a) 1 to 80 wt. %, inclusive, of at least one polypropylene oxide component based on the total weight of the photopolymerizable composition, the polypropylene oxide component comprising i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition. The components (a) through (e) are as discussed in detail above. One or more various optional post-processing steps 840 may be undertaken. Typically, remaining unpolymerized photopolymerizable component may be cured. In certain embodiments, the article comprises an orthodontic article.

Figure 9:
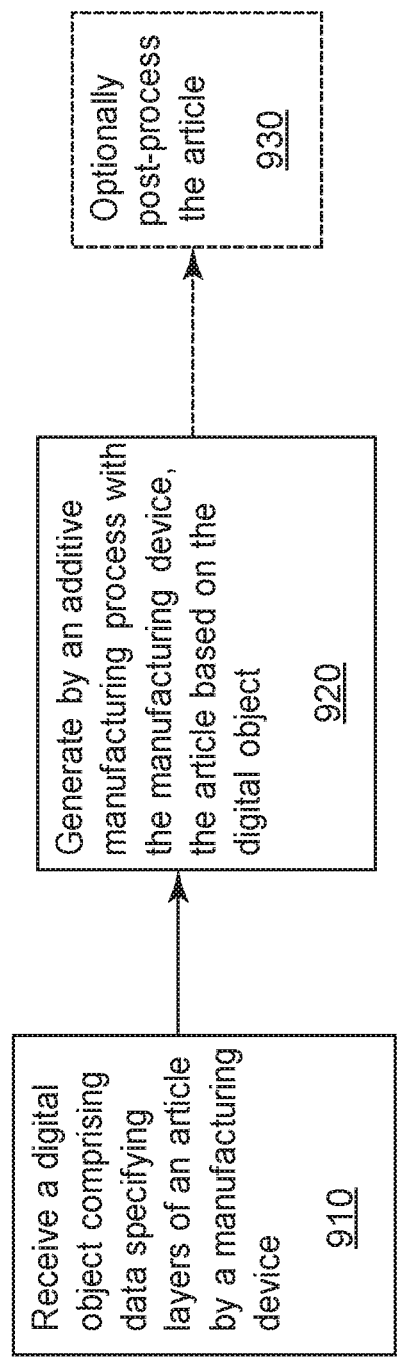
FIG. 9 is a high-level flow chart of an exemplary article additive manufacturing process.

Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930.

Select Embodiments of the Disclosure

Embodiment 1 is a photopolymerizable composition. The photopolymerizable composition includes a blend of (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 2 is the photopolymerizable composition of embodiment 1, wherein the at least one polypropylene oxide component is of Formula I:

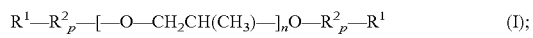

wherein n is an integer in a range of 5 to 70, inclusive; R is a monovalent group of Formula II:

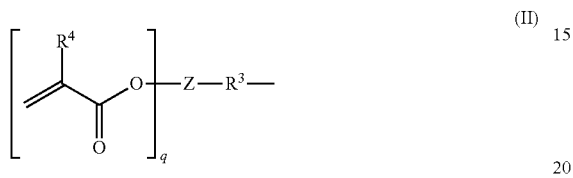

wherein R is selected from H and CH$_3$; Z is a linking group with a valency of q+1; q is 1 or 2; and R$^3$ is a divalent group of Formula III, Formula IV, Formula V, or Formula VI:

wherein R and R$^6$ are independently selected from an alkylene, a heteroalkylene, an alkenediyl, and a heteroalkenediyl;

wherein R$^7$ is an alkylene or an alkenediyl; and R is H, an alkyl, a heteroalkyl, an alkenyl, or a heteroalkenyl;

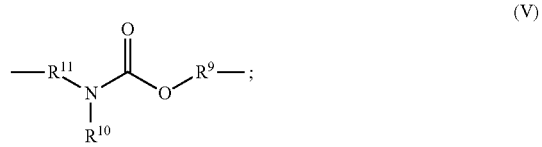

wherein R$^9$ and R$^{11}$ are independently selected from an alkylene, a heteroalkylene, an alkenediyl, and a heteroalkenediyl; and R$^1$ is H, an alkyl, a heteroalkyl, an alkenyl, or a heteroalkenyl; and

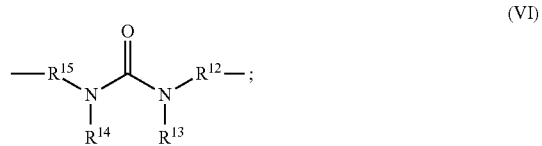

wherein R$^{12}$ and R$^{15}$ are independently selected from an alkylene, a heteroalkylene, an alkenediyl, and a heteroalkenediyl; and R$^{13}$ and R$^{14}$ are independently selected from H, an alkyl, a heteroalkyl, an alkenyl, and a heteroalkenyl; p is 0 or 1; and R$^2$ is of Formula III, Formula IV, Formula V, or Formula VI.

Embodiment 3 is the photopolymerizable composition of embodiment 1 or embodiment 2, wherein the at least one polypropylene oxide component contains iii) at least two functional groups selected from oxycarbonylamino, oxycarbonyl, amino carbonyloxy, carbonyloxy, and combinations thereof.

Embodiment 4 is the photopolymerizable composition of any of embodiments 1 to 3, wherein the at least one polypropylene oxide component is of Formula VII:

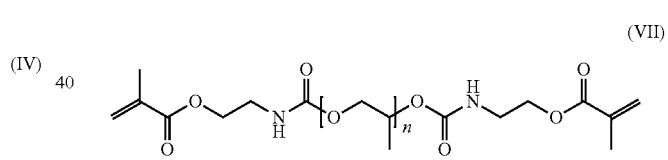

wherein n is 5 to 70.

Embodiment 5 is the photopolymerizable composition of any of embodiments 1 to 3, wherein the at least one polypropylene oxide component is of Formula VIII:

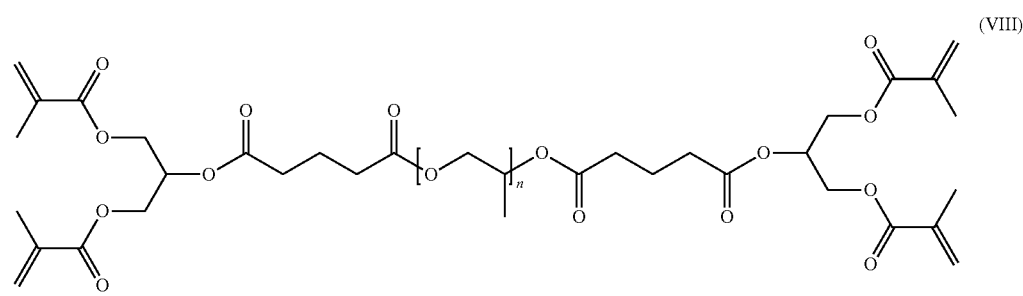

wherein n is 5 to 70 or 5 to 40.

Embodiment 6 is the photopolymerizable composition of any of embodiments 1 to 3, wherein the at least one polypropylene oxide component is of Formula IX:

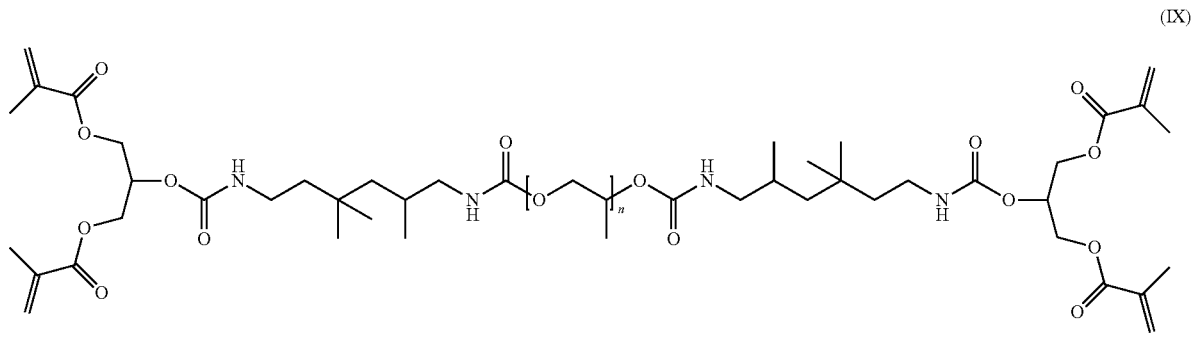

(IX)

wherein n is 5 to 70 or 15 to 20.

Embodiment 7 is the photopolymerizable composition of any of claims 1 to 3 wherein the at least one polypropylene oxide component is of Formula X:

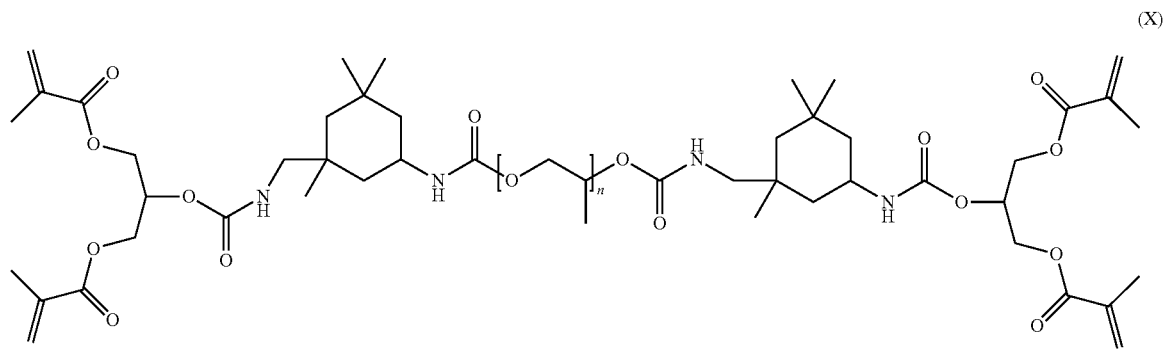

(X)

wherein n is 5 to 70 or 15 to 20.

Embodiment 8 is the photopolymerizable composition of any of embodiments 1 to 3, wherein the at least one polypropylene oxide component is of Formula XI:

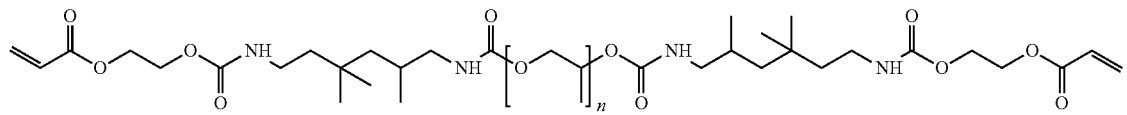

wherein n is 5 to 70 or 15 to 20.

Embodiment 9 is the photopolymerizable composition of any of embodiments 1 to 3, wherein the at least one polypropylene oxide component is of Formula XII:

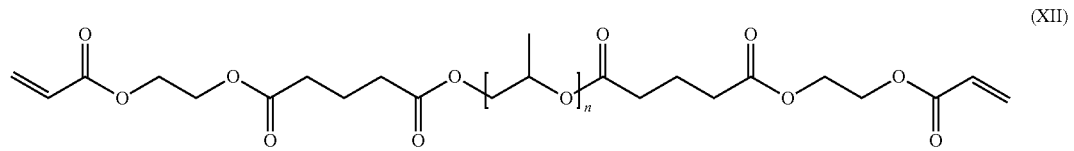

(XII)

wherein n is 5 to 70 or 15 to 20.

Embodiment 10 is the photopolymerizable composition of any of embodiments 1 to 9, wherein the at least one polypropylene oxide component is present in an amount of 10 to 20 wt. %, inclusive.

Embodiment 11 is the photopolymerizable composition of any of embodiments 1 to 10, wherein the at least one urethane component is present and includes a urethane (meth)acrylate, a urethane acrylamide, or combinations thereof, and wherein the at least one urethane component includes a linking group selected from alkyl, polyalkylene, polyalkylene oxide, aryl, polycarbonate, polyester, polyamide, and combinations thereof.

Embodiment 12 is the photopolymerizable composition of any of embodiments 1 to 11, wherein the at least one multifunctional reactive diluent is present and includes a polyester methacrylate.

Embodiment 13 is the photopolymerizable composition of any of embodiments 1 to 12, wherein the at least one initiator includes a photoinitiator, a thermal initiator, or a combination thereof.

Embodiment 14 is the photopolymerizable composition of any of embodiments 1 to 13, wherein the at least one urethane component is present and includes at least one pendant group comprising a photoinitiator.

Embodiment 15 is the photopolymerizable composition of any of embodiments 1 to 14, wherein the polypropylene oxide segment has a molecular weight of 400 to 2,000 grams per mole (g/mol).

Embodiment 16 is the photopolymerizable composition of any of embodiments 1 to 15, further including at least one filler.

Embodiment 17 is the photopolymerizable composition of any of embodiments 1 to 15, further including at least one filler selected from silica, alumina, zirconia, and discontinuous fibers.

Embodiment 18 is the photopolymerizable composition of embodiment 17, wherein the discontinuous fibers include carbon, ceramic, glass, or combinations thereof.

Embodiment 19 is an article. The article includes a reaction product of a photopolymerizable composition. The photopolymerizable composition includes a blend of (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 20 is the article of embodiment 19, wherein the article includes a plurality of layers.

Embodiment 21 is the article of embodiment 19 or embodiment 20, including an orthodontic article.

Embodiment 22 is the article of any of embodiments 19 to 21, exhibiting an elongation at break of 30% or greater.

Embodiment 23 is the article of any of embodiments 19 to 22, exhibiting a tensile strength of 10 MegaPascals (MPa) or greater, as determined according to ASTM D638-10.

Embodiment 24 is the article of any of embodiments 19 to 23, exhibiting a modulus of 50 MPa or greater, as determined according to ASTM D638-10.

Embodiment 25 is the article of any of embodiments 19 to 24, wherein the at least one polypropylene oxide component is of Formula I:

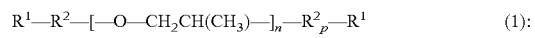

wherein n is an integer in a range of 5 to 70, inclusive; $R^1$ is a monovalent group of Formula II:

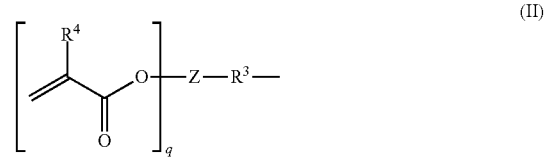

wherein $R^4$ is selected from H and $CH_3$; Z is a linking group with a valency of q+1; q is 1 or 2; and $R^3$ is a divalent group of Formula III, Formula IV, Formula V, or Formula VI:

wherein $R^5$ and $R^6$ are independently selected from an alkylene, a heteroalkylene, an alkenediyl, and a heteroalkenediyl;

wherein $R^7$ is an alkylene or an alkenediyl; and $R^8$ is H, an alkyl, a heteroalkyl, an alkenyl, or a heteroalkenyl;

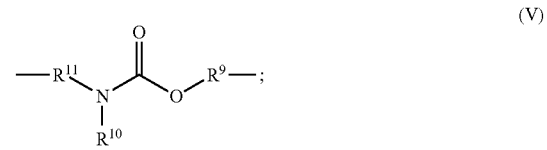

wherein $R^9$ and $R^{11}$ are independently selected from an alkylene, a heteroalkylene, an alkenediyl, and a heteroalkenediyl; and $R^{10}$ is H, an alkyl, a heteroalkyl, an alkenyl, or a heteroalkenyl; and

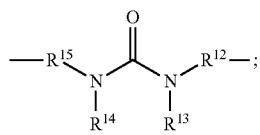
(VI)

wherein $R^{12}$ and $R^{15}$ are independently selected from an alkylene, a heteroalkylene, an alkenediyl, and a heteroalkenediyl; and $R^{13}$ and $R^{14}$ are independently selected from H, an alkyl, a heteroalkyl, an alkenyl, and a heteroalkenyl; p is 0 or 1; and $R^2$ is of Formula III, Formula IV, Formula V, or Formula VI.

Embodiment 26 is the article of any of embodiments 19 to 25, wherein the at least one polypropylene oxide component contains iii) at least two functional groups selected from oxycarbonylamino, oxycarbonyl, amino carbonyloxy, carbonyloxy, and combinations thereof.

Embodiment 27 is the article of any of embodiments 19 to 26, wherein the at least one polypropylene oxide component is of Formula VII:

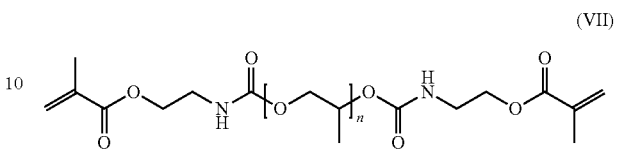
(VII)

wherein n is 5 to 70.

Embodiment 28 is the article of any of embodiments 19 to 26, wherein the at least one polypropylene oxide component is of Formula VIII:

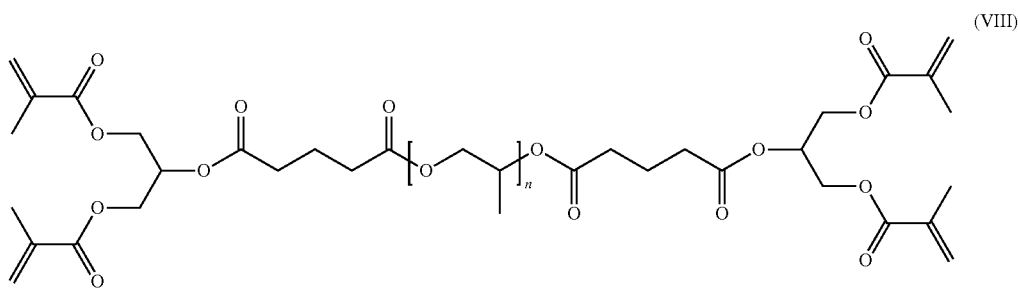
(VIII)

wherein n is 5 to 70 or 5 to 40.

Embodiment 29 is the article of any of embodiments 19 to 26, wherein the at least one polypropylene oxide component is of Formula IX:

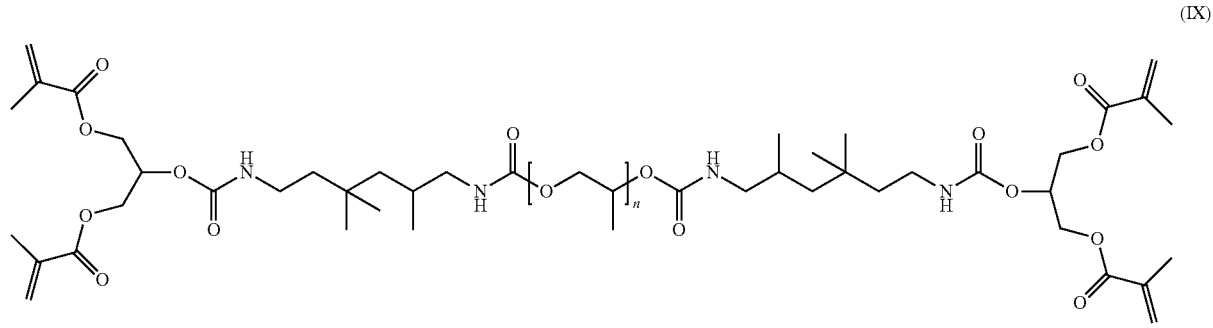
(IX)

wherein n is 5 to 70 or 15 to 20.

Embodiment 30 is the article of any of claims 19 to 26, wherein the at least one polypropylene oxide component is of Formula X:

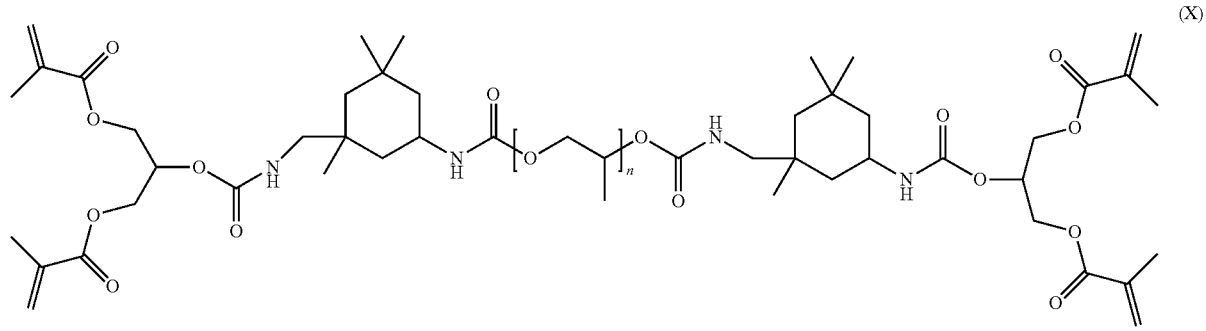

wherein n is 5 to 70 or 15 to 20.

Embodiment 31 is the article of any of embodiments 19 to 26, wherein the at least one polypropylene oxide component is of Formula XI:

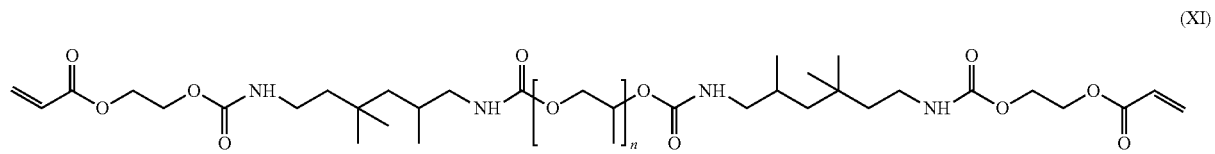

wherein n is 5 to 70 or 15 to 20.

Embodiment 32 is the article of any of embodiments 19 to 26, wherein the at least one polypropylene oxide component is of Formula XII:

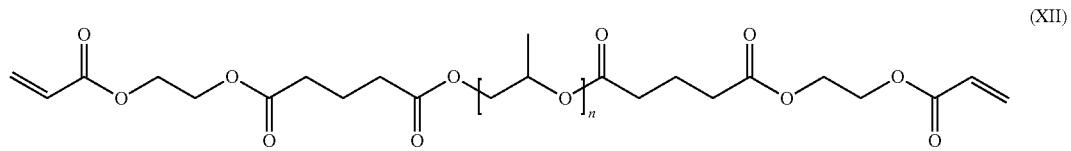

wherein n is 5 to 70 or 15 to 20.

Embodiment 33 is the article of any of embodiments 19 to 32, wherein the at least one polypropylene oxide component is present in an amount of 10 to 20 wt. %, inclusive.

Embodiment 34 is the article of any of embodiments 19 to 33, wherein the at least one urethane component is present and includes a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof.

Embodiment 35 is the article of any of embodiments 19 to 34, wherein the at least one multifunctional reactive diluent is present and includes a polyester methacrylate.

Embodiment 36 is the article of any of embodiments 19 to 35, wherein the at least one initiator includes a photoinitiator, a thermal initiator, or a combination thereof.

Embodiment 37 is the article of any of embodiments 19 to 36, wherein the at least one urethane component is present and comprises at least one pendant group comprising a photoinitiator.

Embodiment 38 is the article of any of embodiments 19 to 37, wherein the at least one urethane component is present and comprises at least one pendant group comprising a photoinitiator.

Embodiment 39 is the article of any of embodiments 19 to 38, wherein the polypropylene oxide segment has a molecular weight of 400 to 2,000 grams per mole (g/mol).

Embodiment 40 is the article of any of embodiments 19 to 39, further including at least one filler.

Embodiment 41 is the article of any of embodiments 19 to 40, further including at least one filler selected from silica, alumina, zirconia, and discontinuous fibers.

Embodiment 42 is the article of embodiment 41, wherein the discontinuous fibers include carbon, ceramic, glass, or combinations thereof.

Embodiment 43 is a method of making an article. The method includes (a) providing a photopolymerizable composition according to the first aspect; (b) selectively curing the photopolymerizable composition to form an article; and optionally (c) curing unpolymerized urethane component, polypropylene oxide component, and/or reactive diluent remaining after step (b). The photopolymerizable composition includes a blend of (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 44 is the method of embodiment 43, further including (d) repeating steps (a) and (b) to form multiple layers and create the article having a three-dimensional structure prior to step (c).

Embodiment 45 is the method of embodiment 43 or embodiment 44, wherein the photopolymerizable composition is cured using actinic radiation including UV radiation, e-beam radiation, visible radiation, or a combination thereof.

Embodiment 46 is the method of embodiment 45, wherein the radiation is directed through a wall of a container holding the photopolymerizable composition.

Embodiment 47 is the method of any of embodiments 43 to 46, wherein the photopolymerizable composition is cured through a floor of a container holding the photopolymerizable composition.

Embodiment 48 is the method of any of embodiments 43 to 47, further including post curing the article using actinic radiation or heat.

Embodiment 49 is the method of any of embodiments 43 to 48, wherein the method includes vat polymerization of the photopolymerizable composition.

Embodiment 50 is the method of any of embodiments 43 to 49, wherein the article includes a film or a shaped integral article.

Embodiment 51 is the method of any of embodiments 43 to 50, wherein the article includes an orthodontic article.

Embodiment 52 is the method of any of embodiments 43 to 51, wherein the article includes one or more channels, one or more undercuts, one or more perforations, or combinations thereof.

Embodiment 53 is the method of any of embodiments 43 to 52, wherein the article has a plurality of layers.

Embodiment 54 is the method of any of embodiments 43 to 53, further including at least one filler.

Embodiment 55 is the method of any of embodiments 43 to 54, further including at least one filler selected from silica, alumina, zirconia, and discontinuous fibers.

Embodiment 56 is the method of embodiment 55, wherein the discontinuous fibers include carbon, ceramic, glass, or combinations thereof.

Embodiment 57 is the method of any of embodiments 43 to 56, wherein the at least one polypropylene oxide component is of Formula I:

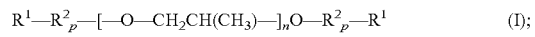

$$R^1-R^2_p-[-O-CH_2CH(CH_3)-]_n O-R^2_p-R^1 \quad (I);$$

wherein n is an integer in a range of 5 to 70, inclusive; R is a monovalent group of Formula II:

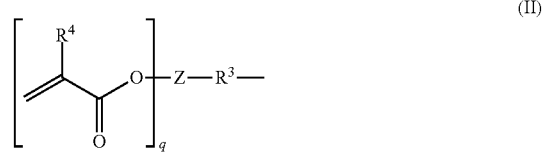

wherein $R^4$ is selected from H and $CH_3$; Z is a linking group with a valency of q+1; q is 1 or 2; and $R^3$ is a divalent group of Formula III, Formula IV, Formula V, or Formula VI:

wherein $R^5$ and $R^6$ are independently selected from an alkylene, a heteroalkylene, an alkenediyl, and a heteroalkenediyl;

wherein $R^7$ is an alkylene or an alkenediyl; and R is H, an alkyl, a heteroalkyl, an alkenyl, or a heteroalkenyl;

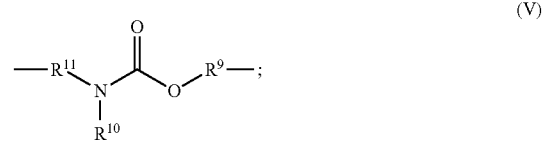

wherein $R^9$ and $R^{11}$ are independently selected from an alkylene, a heteroalkylene, an alkenediyl, and a heteroalkenediyl; and $R^1$ is H, an alkyl, a heteroalkyl, an alkenyl, or a heteroalkenyl; and

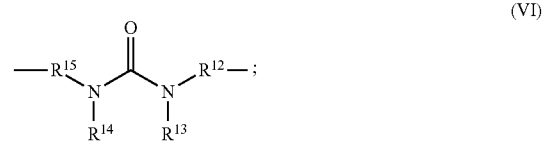

wherein $R^{12}$ and $R^{15}$ are independently selected from an alkylene, a heteroalkylene, an alkenediyl, and a heteroalkenediyl; and $R^{13}$ and $R^{14}$ are independently selected from H, an alkyl, a heteroalkyl, an alkenyl, and a heteroalkenyl; p is 0 or 1; and $R^2$ is of Formula III, Formula IV, Formula V, or Formula VI.

Embodiment 58 is the method of any of embodiments 43 to 57, wherein the at least one polypropylene oxide component comprises iii) at least two functional groups selected from oxycarbonylamino, oxycarbonyl, amino carbonyloxy, carbonyloxy, and combinations thereof.

Embodiment 59 is the method of any of embodiments 43 to 58, wherein the at least one polypropylene oxide component is of Formula VII:

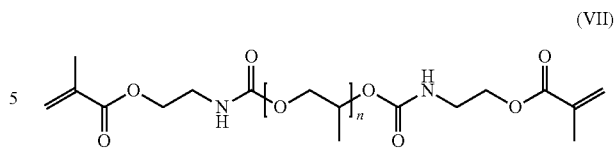

wherein n is 5 to 70.

Embodiment 60 is the method of any of embodiments 43 to 58, wherein the at least one polypropylene oxide component is of Formula VIII:

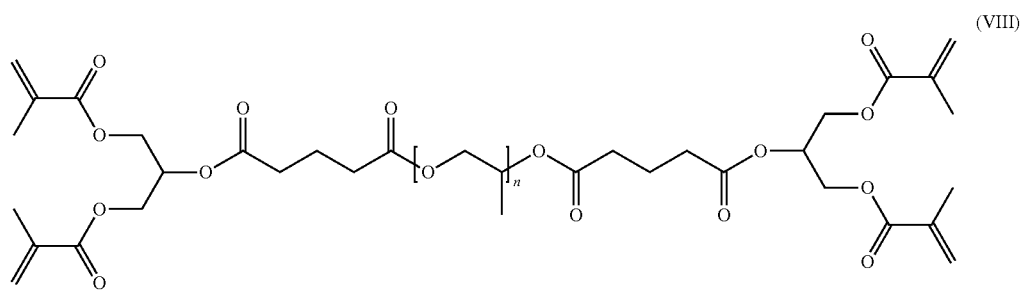

wherein n is 5 to 70 or 5 to 40.

Embodiment 61 is the method of any of embodiments 43 to 58, wherein the at least one polypropylene oxide component is of Formula IX:

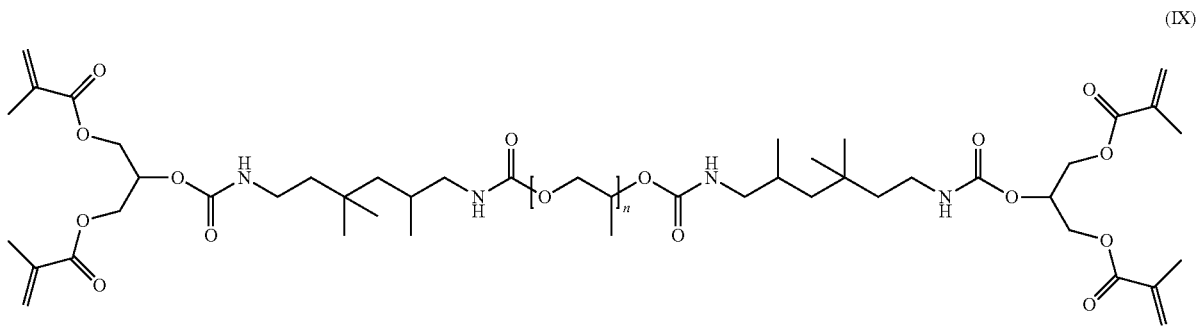

wherein n is 5 to 70 or 15 to 20.

Embodiment 62 is the method of any of claims 43 to 58, wherein the at least one polypropylene oxide component is of Formula X:

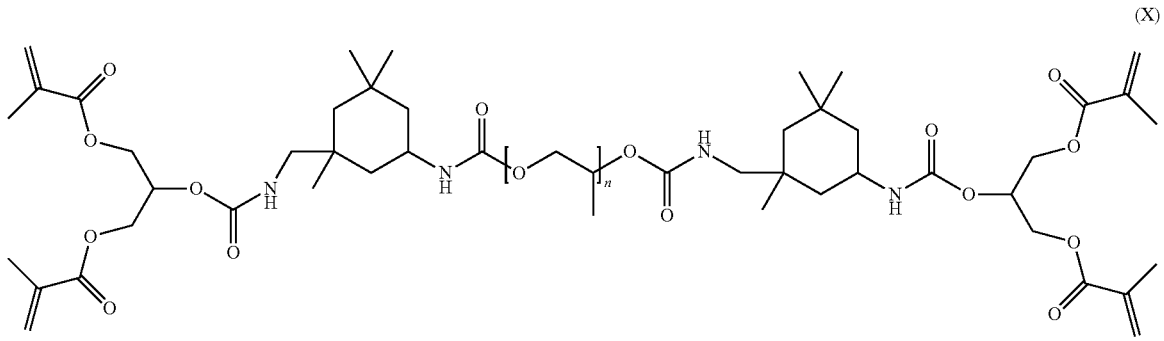

wherein n is 5 to 70 or 15 to 20.

Embodiment 63 is the method of any of embodiments 43 to 58, wherein the at least one polypropylene oxide component is of Formula XI:

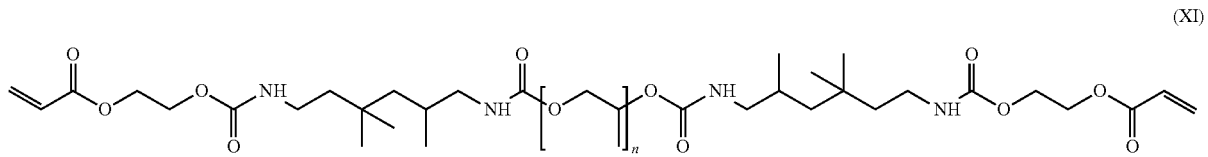

wherein n is 5 to 70 or 15 to 20.

Embodiment 64 is the method of any of embodiments 43 to 58, wherein the at least one polypropylene oxide component is of Formula XII:

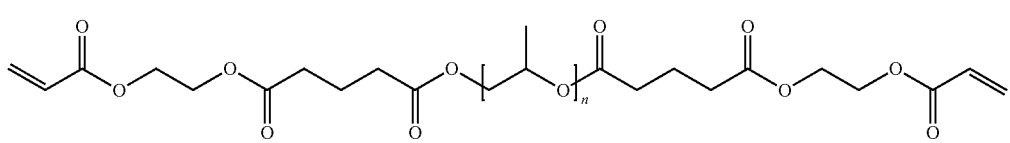

wherein n is 5 to 70 or 15 to 20.

Embodiment 65 is the method of any of embodiments 43 to 64, wherein the at least one polypropylene oxide component is present in an amount of 10 to 20 wt. %, inclusive.

Embodiment 66 is the method of any of embodiments 43 to 65, wherein the at least one urethane component is present and includes a urethane (meth)acrylate, a urethane acrylamide, or combinations thereof, and wherein the at least one urethane component contains a linking group selected from alkyl, polyalkylene, polyalkylene oxide, aryl, polycarbonate, polyester, polyamide, and combinations thereof.

Embodiment 67 is the method of any of embodiments 43 to 66, wherein the at least one multifunctional reactive diluent is present and includes a polyester methacrylate.

Embodiment 68 is the method of any of embodiments 43 to 67, wherein the at least one initiator includes a photoinitiator, a thermal initiator, or a combination thereof.

Embodiment 69 is the method of any of embodiments 43 to 68, wherein the at least one urethane component is present and comprises at least one pendant group comprising a photoinitiator.

Embodiment 70 is the method of any of embodiments 43 to 69, wherein the polypropylene oxide segment has a molecular weight of 400 to 2,000 grams per mole (g/mol).

Embodiment 71 is a non-transitory machine readable medium. The non-transitory machine readable medium includes data representing a three-dimensional model of an article, when accessed by one or more processors interfacing with a 3D printer, causes the 3D printer to create an article comprising a reaction product of a photopolymerizable composition. The photopolymerizable composition includes a blend of: (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 72 is a method. The method includes (a) retrieving, from a non-transitory machine readable medium, data representing a 3D model of an article; (b) executing, by one or more processors, a 3D printing application interfacing with a manufacturing device using the data; and c) generating, by the manufacturing device, a physical object of the article, the article comprising a reaction product of a photopolymerizable composition. The photopolymerizable composition includes a blend of (a) 1 to 80 wt. %, inclusive, of at least one polypropylene oxide component based on the total weight of the photopolymerizable composition, the polypropylene oxide component including i) two (meth) acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 73 is an article generated using the method of embodiment 72.

Embodiment 74 is the article of embodiment 73, wherein the article includes an orthodontic article.

Embodiment 75 is a method. The method includes (a) receiving, by a manufacturing device having one or more processors, a digital object comprising data specifying a plurality of layers of an article; and (b) generating, with the manufacturing device by an additive manufacturing process, the article based on the digital object, the article comprising a reaction product of a photopolymerizable composition. The photopolymerizable composition includes a blend of: (a) 1 to 80 wt. %, inclusive, of at least one polypropylene oxide component based on the total weight of the photopolymerizable composition, the polypropylene oxide component including i) two (meth)acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 76 is the method of embodiment 75, wherein the article includes an orthodontic article.

Embodiment 77 is a system. The system includes a display that displays a 3D model of an article; and one or more processors that, in response to the 3D model selected by a user, cause a 3D printer to create a physical object of an article, the article comprising a reaction product of a photopolymerizable composition. The photopolymerizable composition includes a blend of: (a) 1 to 80 wt. %, inclusive, of at least one polypropylene oxide component based on the total weight of the photopolymerizable composition, the polypropylene oxide component including i) two (meth) acryl groups; ii) one polypropylene oxide segment; and iii) at least two functional groups selected from oxycarbonylamino, oxycarbonyl, amino carbonyloxy, carbonyloxy, amino carbonylamino, aminocarbonyl, carbonylamino, and combinations thereof. The photopolymerizable composition optionally further includes (b) 30 wt. % or greater of at least one urethane component, if present, based on the total weight of the photopolymerizable composition; with the proviso that when the at least one urethane component is not present the at least one polypropylene oxide component includes at least two functional groups selected from oxycarbonylamino, amino carbonyloxy, and combinations thereof. Additionally, the photopolymerizable composition optionally includes (c) at least one multifunctional reactive diluent in an amount of 1 to 30 wt. %, inclusive, if present, based on the total weight of the photopolymerizable composition. The photopolymerizable composition also includes (d) 0.1 to 5 wt. %, inclusive, of at least one initiator; and (e) an optional inhibitor in an amount of 0.001 to 1 wt. %, inclusive, if present, based on the total weight of the photopolymerizable composition.

EXAMPLES

Objects and advantages of this disclosure are further illustrated by the following examples, but the particular materials and amounts thereof recited in these examples, as well as other conditions and details, should not be construed to unduly limit this disclosure.

The materials used in the following examples are summarized in Table 1.

TABLE 1

Materials.

| | Description | Source | Functionality |
|---|---|---|---|
| Crosslinking components: | | | |
| Exothane 108 (EXO 108) | Urethane (meth)acrylate oligomer | Esstech Inc, (Essington, PA, USA) | 2 |
| Exothane 10 (EXO 10) | Urethane (meth)acrylate oligomer | Esstech Inc, (Essington, PA, USA) | 2 |
| TEGDMA | Triethyleneglycol dimethacrylate | Sigma-Aldrich (St. Louis, MO) | 2 |
| D-Zethacrylate | Ethoxylated(4) bisphenol-A dimethacrylate | synthesized | 2 |
| IBuMA | Isobutyl Methacrylate | TCI America, (Portland OR, USA) | 1 |
| HEMA | Hydroxyethyl Methacrylate | Esstech Inc (Essington, PA, USA) | 1 |
| EHMA | Ethyl hexyl methacrylate | Alfa Aesar, (Haverhill, MA, USA) | 1 |
| Additives: | | | |
| BHT | 2,6-Di-tert-butyl-4-methyl-phenol | Fluka Analytical (St. Louis, MO) | |
| TINOPAL OB (TinOB) | 2,5-Thiophenediyl-bis(5-tert-butyl-1,3-benzoxazole) (optical brightener) | BASF, Wyandotte, MI | — |
| IRGAGURE TPO (TPO) | 2,4,6-Trimethylbenzoyldiphenyl phosphine oxide (photoinitiator) | BASF (Wyandotte, MI) | — |

A number of PPO Oligmers were synthesized for use as a reactive diluent. The PPO oligomers are designed to help reduce the overall viscosity of the printing formulation without making the final article too stiff or brittle.

Example 1: Preparation of Polypropylene Oxide-1000 Diurethane Dimethacrylate (PPO-1000 DUDMA)

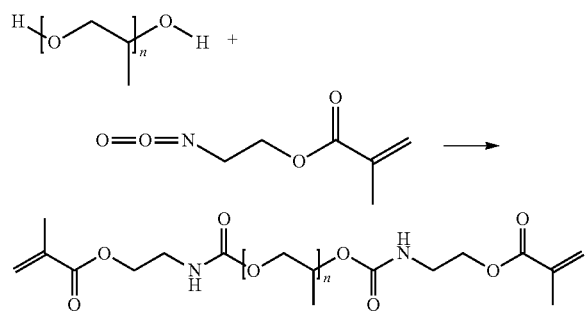

Polypropylene oxide-1000 (PPO-1000, 43.1 grams, 43.1 mmol, Alfa Aesar, Tewksbury, MA, 01876, USA) was placed in a 100-mL glass jar followed by butylated hydroxytoluene (BHT, 0.050 grams, Sigma Aldrich, St Louis, MO, USA) and dibutyltin dilaurate catalyst (0.5 grams, Sigma Aldrich, St Louis, MO, USA). The jar contents were hand mixed using a Teflon stick until solutes were completely dissolved. 2-Isocyanatoethyl methacrylate (IEM, 13.1 grams, 84.4 mmol, Show Denko America Inc., New York, NY, USA) was added incrementally in 5 minute intervals with mixing between additions. After complete addition and cooling to room temperature, the jar was placed in an oven at 60° C. for 1 hour with mixing every 10-15 minutes.

Reaction completion was confirmed by disappearance of the isocyanate (NCO) band around 2250-2275 $cm^{-1}$ using an FTIR spectrophotometer. The structure of desired product was also confirmed by $^1H$ and $^{13}C$ NMR run on a 500 MHz NMR spectrophotometer.

The viscosity at 22° C., 35° C., 40° C., and 50° C. was measured using a Brookfield CAP 2000+ viscometer with a cone and plate assembly.

TABLE 2

Example 1 Viscosity.

| Temperature (° C.) | Viscosity η (Pa*s) | Torque (%) |
|---|---|---|
| 22 | 1.55 | 12.4 |
| 35 | 0.53 | 11.3 |
| 40 | 0.375 | 16 |
| 50 | 0.206 | 13.2 |

Example 2: Preparation of Polypropylene Oxide-400 Diurethane Dimethacrylate (PPO-400 DUDMA)

Polypropylene oxide-400 (PPO-400, 33.11 grams, 83 mmol, Alfa Aesar, Tewksbury, MA, 01876, USA) was placed in a 100-mL glass jar followed by butylated hydroxytoluene (BHT, 0.050 grams, Sigma Aldrich, St Louis, MO, USA) and dibutyltin dilaurate catalyst (0.5 grams, Sigma Aldrich, St Louis, MO, USA). The jar contents were hand mixed until solutes were completely dissolved. 2-Isocyanatoethyl methacrylate (IEM, 25.51 grams, 164 mmol, Show Denko America Inc, New York, NY, USA) was added incremental in 5 minute intervals with mixing between additions. After complete addition and cooling to room temperature, the jar was placed in an oven at 60° C. for 1 hour with mixing every 1-15 minutes. Reaction completion was confirmed by disappearance of the isocyanate (NCO) band around 2250-2275 cm$^{-1}$ using an FTIR spectrophotometer. The structure of desired product was confirmed by $^1$H and $^{13}$C NMR run on a 500 MHz NMR spectrophotometer and FTIR The viscosity at 22, 35, 40 and 50° C. was measured using a Brookfield CAP 2000+ viscometer with a cone and plate assembly:

TABLE 3

Example 2 Viscosity.

| Temperature (° C.) | Viscosity η (Pa*s) | Torque (%) |
|---|---|---|
| 22 | 2.98 | 15.9 |
| 35 | 0.781 | 12.5 |
| 40 | 0.516 | 16.5 |
| 50 | 0.252 | 16 |

Example 3: Preparation of Polypropylene Oxide-4,000 Diurethane Dimethacrylate (PPO-4000 DUDMA)

Polypropylene oxide-4,000 (PPO-4,000, 360 grams, 90 mmol, Alfa Aesar, Tewksbury, MA, 01876, USA) was placed in a 500-mL glass jar followed by butylated hydroxytoluene (BHT, 0.20 grams, Sigma Aldrich, St Louis, MO, USA) and dibutyltin dilaurate catalyst (0.5 grams, Sigma Aldrich, St Louis, MO, USA). The jar contents were hand mixed until solutes were completely dissolved. 2-Isocyanatoethyl methacrylate (IEM, 27.6 grams, 178 mmol, Showa Denko America Inc., New York, NY, USA) was added incremental in 5 minutes intervals with mixing between additions. After complete addition and cooling to room temperature, the jar was placed in an oven at 60° C. for 1 hour with mixing every 1-15 minutes. Reaction completion was confirmed by disappearance of the isocyanate (NCO) band around 2250-2275 cm$^{-1}$ using an FTIR spectrophotometer. The structure of desired product was confirmed by $^1$H and $^{13}$C NMR run on a 500 MHz NMR spectrophotometer and FTIR.

The viscosity was measured at 25° C. and shear rate of 1.000 using ARG2 rheometer and found η=0.532 Pa*s.

Example 4: Preparation of Glutaric Acid Glycidyldimethacrylate Monoester

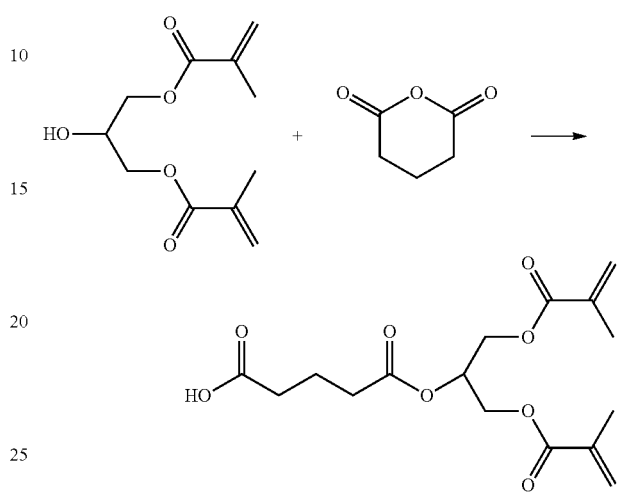

Glutaric anhydride (120.55 grams, 1,057 mmol, Alfa Aesar, Tewksbury, MA, 01876, USA) and glycidyl dimethacrylate (GDMA, 241.6 grams, 1,059 mmol, TCI America, Portland, OR, USA) were dissolved in acetonitrile (380 mL, EMD Millipore, Billerica, MA, USA) in a 1 L 3-neck flask equipped with a mechanical stirrer, a thermocouple and a condenser. The flask contents were heated to reflux with a continuous stirring overnight. The next day, the solvent was removed in a rotary evaporator with a bath temperature 50° C. The obtained product was further dried at 80-90° C. under a vacuum pump with air bleeding to give a colorless liquid with 94% yield. Product structure was confirmed by $^1$H NMR spectrum recorded in a 500 MHz machine.

Example 5: Preparation of Polypropylene Oxide-2,000 Bis(Glutaryl Glycidyldimethacrylate) Ester (PPO-2000 BGGDMA)

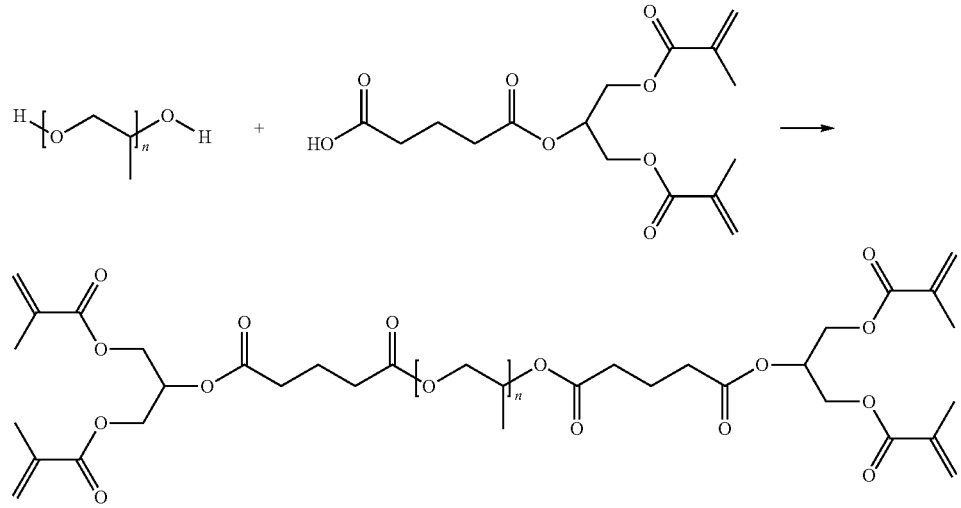

Polypropylene oxide-2,000 (PPO-2,000, 101 grams, 50.5 mmol, Alfa Aesar, Tewksbury, MA, 01876, USA) and glutaric acid glycidyldimethacrylate mono-ester (36.4 grams, 106 mmol) were dissolved in toluene (300 mL, GFS Chemicals Inc., Powell, OH, USA) in a 1-L 3-neck flask equipped with a mechanical stirrer, a dropping funnel, a thermocouple, water bath, a $N_2$ atmosphere. To the mixture was added 4-N,N-dimethlyamino pyridine (DMAP, 2.3 grams, Alfa Aesar, Tewksbury, MA, 01876, USA). With vigorous stirring, the flask was cooled in an ice bath to 1-5° C. Then a solution of dicyclohexylcarbodiimide (DCC, 21 grams, 102 mmol Alfa Aesar, Tewksbury, MA, 01876, USA) in toluene (150 mL) was added drop-wise over 45 minutes. The mixture was then stirred at the cold temperature for 2 hours and room temperature overnight.

The next day, any solid formed was removed by vacuum filtration. The filtrate was washed with 1N HCl solution (1×100 mL), 10% aqueous sodium bicarbonate (1×100 mL) and water (1×200 mL). The organic layer was dried (using $Na_2SO_4$), then concentrated in a rotary evaporator with a water bath temperature of 45-50° C. to give a colorless liquid with a very small amount of a fine solid carried in from previous steps. The flask and contents were left on bench at room temperature overnight. Any additional solid formed was removed by vacuum filtration. Residual solvent was then removed under vacuum at 90° C. with air bleeding. The product was obtained as a colorless clear liquid with a minor haze. The structure of the product was confirmed by recording $^1H$ and $^{13}C$ NMR in a 500 MHz Machine.

Example 6: Preparation of Polypropylene Oxide-400 Bis(Glutaryl Glycidyldimethacrylate) Ester (PPO-400 BGGDMA)

Polypropylene oxide-400 (PPO-400, 127.49 grams, 319 mmol, Alfa Aesar, Tewksbury, MA, 01876, USA) and glutaric acid glycidyldimethacrylate mono-ester (215 grams, 628 mmol) were dissolved in ethyl acetate (250 mL, GFS Chemicals Inc., Powell, OH, USA) in a 1-L 3-neck flask equipped with a mechanical stirrer, a dropping funnel, a thermocouple, water bath, a $N_2$ atmosphere. To the mixture was added 4-N,N-dimethlyamino pyridine (DMAP, 5.3 grams, 43 mmol, Alfa Aesar, Tewksbury, MA, 01876, USA). With vigorous stirring, the flask was cooled in an ice bath to 1-5° C. Then a solution of dicyclohexylcarbodiimide (DCC, 128.5 grams, 623 mmol, Alfa Aesar, Tewksbury, MA, 01876, USA) in ethyl acetate (250 mL) was added drop-wise over 45 minutes. The mixture was then stirred at the cold temperature for 2 hours and room temperature overnight.

The next day, any solid formed was removed by vacuum filtration. The filtrate was washed with 1N HCl solution (1×100 mL), 10% aqueous sodium bicarbonate (1×100 mL) and water (1×200 mL). The organic layer was dried (using $Na_2SO_4$) then concentrated in a rotary evaporator with a water bath temperature of 45-50° C. to give a colorless liquid with a very small amount of a fine solid carried in from previous steps. The flask and contents were left on bench at room temperature overnight. Any additional solid formed was removed by vacuum filtration. Residual solvent was then removed under vacuum at 90° C. with air bleeding. The product was obtained as a colorless clear liquid with a minor haze. The reaction yield was 85.3%. The structure of the product was confirmed by recording $^1H$ and $^{13}C$ NMR in a 500 MHz Machine.

The viscosity was measured at 25° C. and shear rate of 1.000 using ARG2 rheometer and found $\eta$=0.5576 Pa*s.

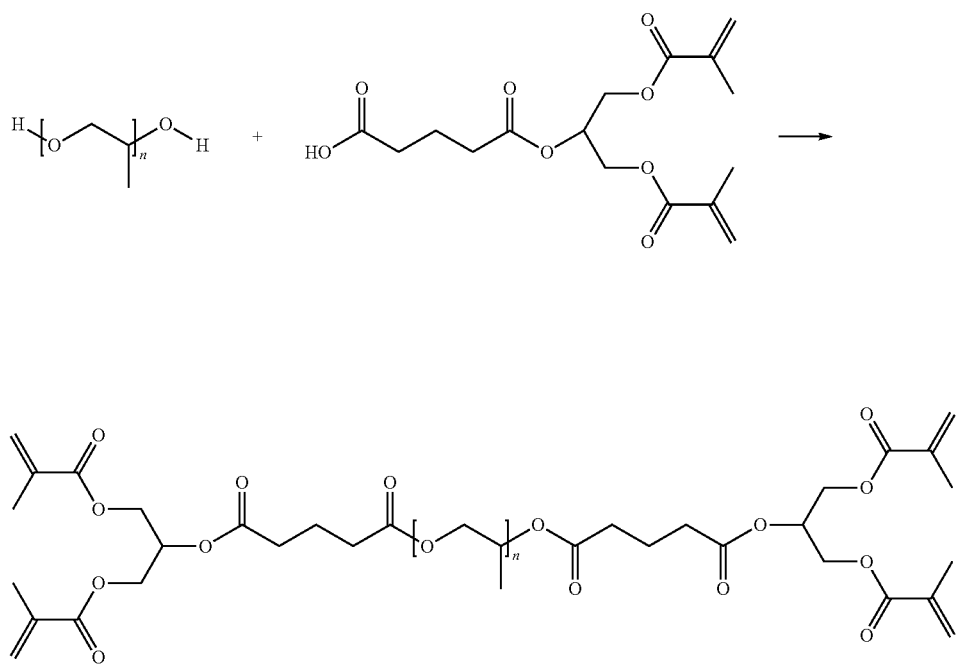

Example 7: Polypropylene Oxide-1,000 Tetraurethane Tetramethacrylate Using TMHDI (PPO-1000 TMHDI TMA)

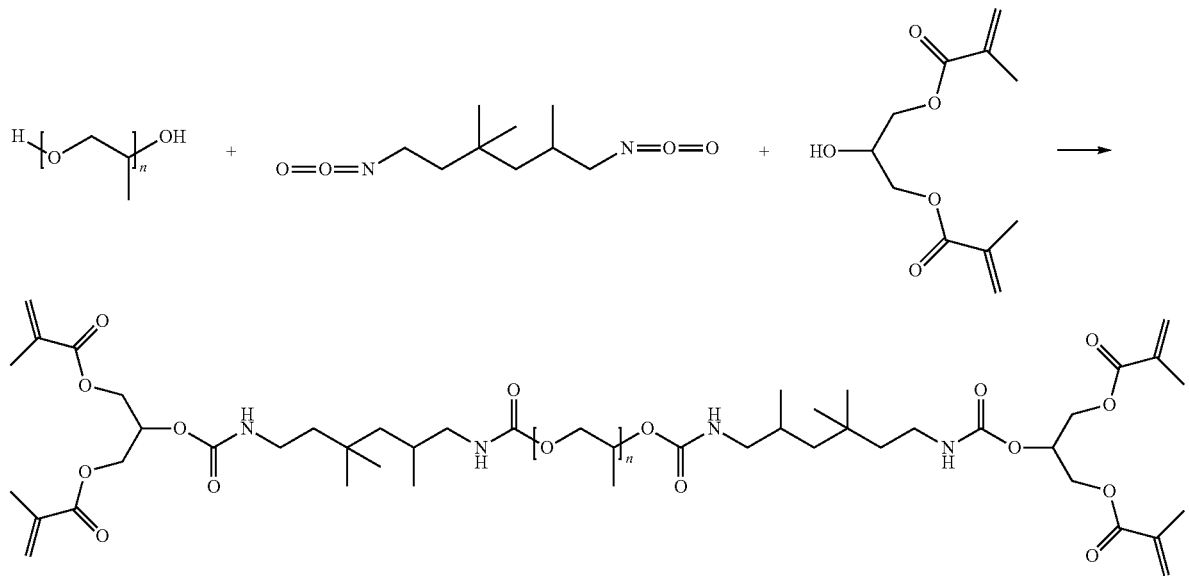

Trimethylhexamethylene diisocyanate (25.15 grams, 119.5 mmol, TCI America, Portland, OR, USA) was placed in a 500-mL glass jar with BHT (0.120 g). In a separate 500 mL glass jar, Polypropylene oxide-1000 (PPO-1000, 60.1 grams, 60.1 mmol, Alfa Aesar, Tewksbury, MA, 01876, USA) was mixed with dibutyltin dilaurate (0.5 grams, Sigma Aldrich, St Louis, MO, USA). The PPO-1,000 mix was added in small increments with hand shaking to the di-isocyanate present in the other jar at a rate that insured mild exotherm. After complete addition, the jar was left on bench till cooled to room temperature.

Glycidyl dimethacrylate (GDMA, 27.5 grams, 120 mmol) was then added to the jar and mixing by swirling. The jar was left to stand on the bench with mixing every 15-20 minutes for a couple of hours. The next day, IR was recorded and there was still some residual NCO. The jar was placed in an oven at 65-70° C. with hand mixing every 15 minutes for 1 hour. IR spectrum was re-taken which indicated complete reaction since the band corresponding to NCO completely disappeared. NMR was also recorded on a 500 MHz machine which confirmed the structure.

The viscosity was measured at 25° C. and shear rate of 1.000 using ARG2 rheometer and found η=42.46 Pa*s.

Example 8: Polypropylene Oxide-1,000 Tetraurethane Tetramethacrylate Using IPDI (PPO-1000 IPDI TMA)

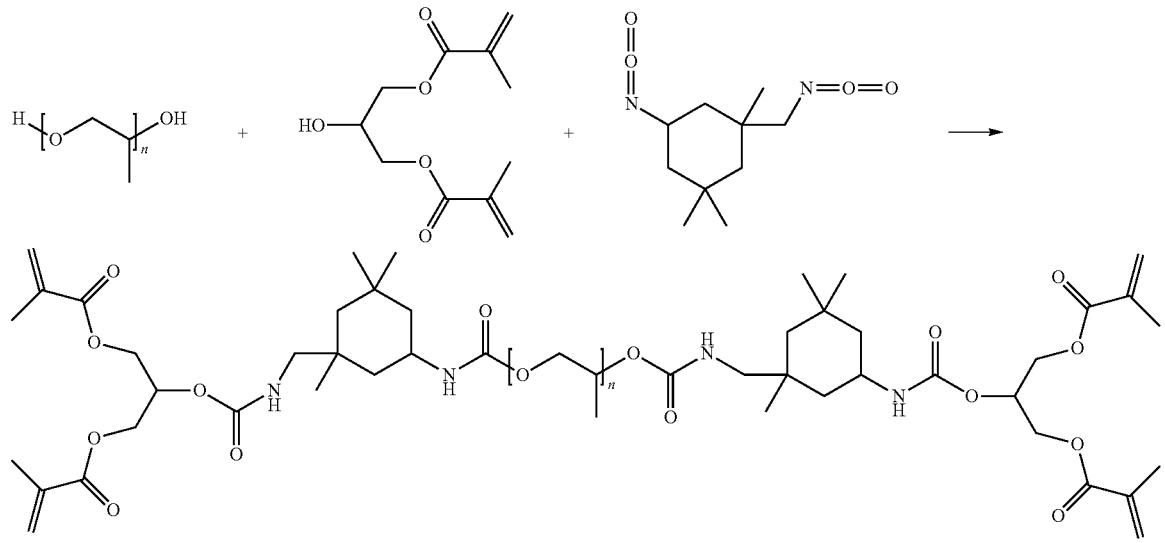

Isophorone diisocyanate (IPDI, Alfa Aesar, Tewksbury, MA, 01876, USA) was placed in a glass jar with BHT. In a separate 500 mL glass jar, Polypropylene oxide-1000 (PPO-1000, Alfa Aesar, Tewksbury, MA, 01876, USA) was mixed with dibutyltin dilaurate (Sigma Aldrich, St Louis, MO, USA). The PPO-1,000 mix was added in small increments with hand shaking to the di-isocyanate present in the other jar at a rate that insured mild exotherm. After complete addition, the jar was left on bench until cooled to room temperature.

Glycidyl dimethacrylate (GDMA), was then added to the jar and mixing by swirling. The jar was left to stand on the bench with mixing every 15-20 minutes for a couple of hours. The jar was placed in an oven at 65-70° C. with hand mixing every 15 minutes for 1 hour. IR spectrum was re-taken which indicated complete reaction since the band corresponding to NCO completely disappeared. NMR was also recorded on a 500 MHz machine which confirmed the structure.

Example 9: Polypropylene Oxide-1,000 Tetraurethane Dimethacrylate Using TMHDI. (PPO-1000 TMHDI DA)

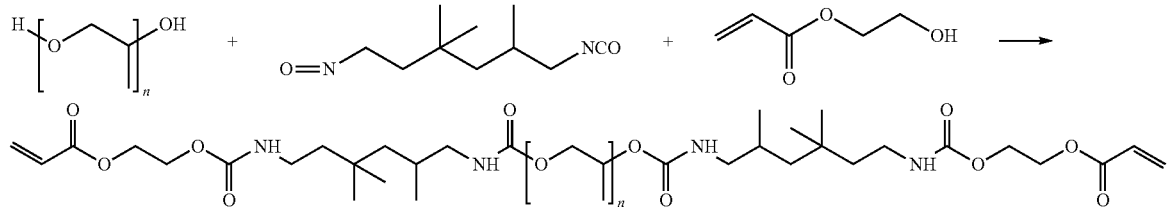

This example was prepared following the procedure for the tetramers above in Example 7, with a slight modification.

Trimethylhexamethylene diisocyanate was dissolved in dichloromethane (CH₂Cl₂, 500 mL, Alfa Aesar, Tewksbury, MA, 01876, USA) in a 1-Liter round bottom flask equipped with a magnetic stirring bar and a N₂ stream. Dibutyltin dilaurate was added. With continuous stirring at room temperature, a solution of 2-hydroxyethyl acrylate (HEA, Alfa Aesar, Tewksbury, MA, 01876, USA)) in CH₂Cl₂ (50 ml) was added in small increments. After complete addition, the contents were stirred at room temperature for 1 hour. The solvent was removed in a rotary evaporator at 30° C. Further drying was done by placing the flask under vacuum pump overnight. NMR was recorded and showed the desired product. The viscosity was measured at 25° C. and shear rate of 1.000 using ARG2 rheometer and found q=8.388 Pa*s.

Example 10: Preparation of 2-Acryloyloxyethyl Glutarate

2-Hydroxyethylacrylate (HEA, 150.25 grams, 1,293 mmol, Alfa Aesar, Tewksbury, MA, 01876, USA) was placed in a 500-mL 3-neck round bottom flask equipped with a thermocouple connected to a temperature controller, a mechanical stirrer and an air line that was connected to a bubbler. HEA was heated slowly to 100° C., and during this time glutaric anhydride (147.6 grams, 1,294 mmol, TCI America, Portland, OR, USA) was added in 4-5 increments over 30 minutes. The result was a clear solution. Stirring and heating at 100° C. were continued for 5 hours. The heat was then turned off. NMR was recorded on a 500 MHz machine and showed that reaction reached completion with the desired product obtained.

Example 11: Preparation of Polypropylene Oxide-1,000 Bis(2-Acryloyloxyethylgutaryl) Ester. (PPO-1000 Ester DA)

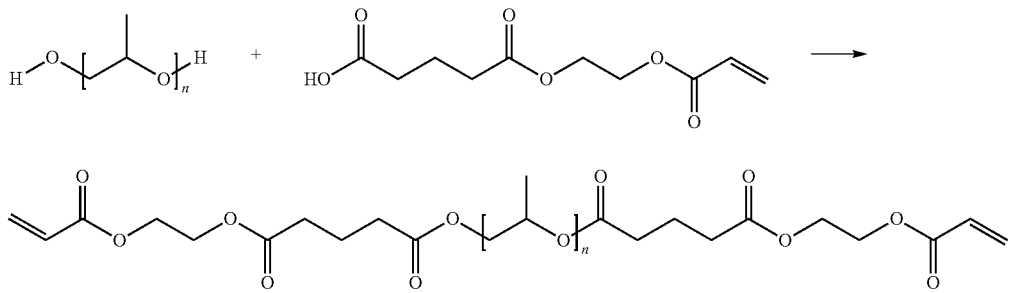

The preparation was carried out following the procedure described in Example 5 above using Polypropylene oxide-1,000 (PPO-1,000 from Dow Chemical, Midland, MI USA) and 2-acryloyloxyethyl glutarate (HEA glutarate). The prod uct structure was confirmed by NMR. The viscosity was measured at 25° C. and shear rate of 1.000 using ARG2 rheometer and 1=0.3185 Pa*s.

Examples E12-E24: Photocurable Compositions Based on Novel PPO Oligomers

The Example 12 (E12) formulation shown in Table 4 below was mixed in a glass jar. The E12 mixture was placed on a rolling mixer to make a homogenous mixture. The mixture was degassed by speed mixing in a Thinky planetary mixer under vacuum and 2000 rpm for 1 minute. The mixture was then poured in a silicone dog-bone mold (Type V mold, ASTM D638). The filled mold was placed between two glass plates and cured in a broad-spectrum UV chamber (Dymax Light Curing Systems Model 2000 Flood) for 5 minutes. The sample was demolded and cured for another 5 minutes in the chamber. These dog-bones were tested on an Insight MTS with 5 kN load cell at the rate of 5 mm/minute. The samples were not strain gauged and the elongation to break was obtained from the crosshead movement. The gauge length of 9.53 mm was used for calculation of strain. Five replicate samples were tested. The tensile strength, tensile modulus and elongation at break of the samples were determined and shown in Table 5 below. Subsequent examples, E13-E23, were made similarly (the formulations are summarized in Table 4 below) and mechanical properties are summarized in Table 5. Comparative Examples CE1, CE2, CE3, and CE4 were prepared and tested in the same manner.

TABLE 5

Mechanical Properties of photocurable formulations with PPO oligomers

| Sample ID | Tensile strength (Std Dev) MPa | Elongation to break (Std Dev) MPa |
| --- | --- | --- |
| CE1 | 61.44 (0.94) | 27.8 (10.3) |
| CE2 | 28.94 (2.3) | 91 (14.5) |
| CE3 | Not compatible | Not compatible |
| CE4 | Incompatible, turns hazy | Incompatible, turns hazy |
| E12 | 10.6 (1.1) | 103.5 (9.2) |
| E13 | 42.2 (2.9) | 45.9 (10.6) |
| E14 | 37.6 (3.1) | 83.6 (10.7) |
| E15 | 39 (3.5) | 43.8 (22) |
| E16 | 38.7 | 35.3 |
| E17 | 25.7 (2.7) | 42.6 (10.7) |
| E18 | 31.5 (1.4) | 49.8 (11.7) |
| E19 | 32.5 (3.1) | 75.6 (13.2) |
| E20 | 31.7 (3.6) | 60.8 (16.6) |
| E21 | 6.3 (0.6) | 65.9 (11.2) |
| E22 | 30.2 (1.6) | 102.9 (7.6) |
| E23 | 20.3 (2.1) | 44.1 (15.1) |
| E24 | 30.4 (2.1) | 94.0 (23.4) |

As seen from the Examples above, the addition of PPO oligomers substantially increases the elongation to break while maintaining acceptable strength of the material. It is possible to make rigid to elastomeric materials by selecting particular ratios of the formulation.

TABLE 4

Photocurable Formulations with PPO Oligomers (parts)

| Ex. | EXO 10 | EXO 108 | TEG DMA | PPO 400 | PPO 1000* | PPO 2000 | PPO 4000 | TPO | BHT | TinOB |
| --- | --- | --- | --- | --- | --- | --- | --- | --- | --- | --- |
| CE1 | 80 | — | 20 | — | — | — | — | 1 | 0.1 | 0.1 |
| CE2 | — | 80 | 20 | — | — | — | — | 1 | 0.1 | 0.1 |
| CE3 | 50 | — | — | — | — | — | 50 | 1 | 0.1 | 0.1 |
| CE4 | 60 | — | 10 | — | — | 30 | — | 1 | 0.1 | 0.1 |
| E12 | 50 | — | — | — | 50 (Ex. 1) | — | — | 1 | 0.1 | 0.1 |
| E13 | 70 | — | 20 | — | 10 (Ex. 1) | — | — | 1 | 0.1 | 0.1 |
| E14 | 70 | — | 10 | — | 20 (Ex. 1) | — | — | 0.5 | 0.025 | 0.025 |
| E15 | 70 | — | 10 | 10 (Ex. 2) | 10 (Ex. 1) | — | — | 0.5 | 0.025 | 0.025 |
| E16 | 70 | — | 10 | 20 (Ex. 6) | — | — | — | 0.5 | 0.025 | 0.025 |
| E17 | — | — | 20 | — | 80 (Ex. 8) | — | — | 0.5 | 0.025 | 0.025 |
| E18 | 70 | — | 10 | — | 20 (Ex. 8) | — | — | 0.5 | 0.025 | 0.025 |
| E19 | 70 | — | 10 | — | 20 (Ex11) | — | — | 0.5 | 0.025 | 0.025 |
| E20 | — | 60 | 25 | — | 15 (Ex. 8) | — | — | 0.5 | 0.025 | 0.025 |
| E21 | — | 50 | — | — | — | 50 | — | 0.5 | 0.025 | 0.025 |
| E22* | 65 | — | 5 | — | 20 (Ex. 1) | — | — | 0.5 | 0.05 | 0.05 |
| E23 | 35 | 35 | 10 | — | — | 20 | — | 0.5 | 0.05 | 0.05 |

*Example E22 also contained 10 parts of D-zethacrylate.

Example E24 was prepared in the same fashion as examples E12-E23 except with the following components and amounts: 47.5 parts of Exothane 10, 15.84 parts of IBuMA, 1.8 parts of EHMA, 15.84 parts of HEMA, 5 parts of PPO 400 (Ex. 6), 0.5 parts of TPO, 0.025 parts of BHT, and 0.025 parts of TinOB.

Example 25: Printing of Orthodontic Clear Tray Aligner

The formulation of E22 was photopolymerized on the Asiga PICO2 HD vat polymerization 3D printer with a LED light source of 385 nm and ~16 mW/cm$^2$ of power, available from Asiga USA, Anaheim Hills, CA.

An STL file of the aligner was loaded into the software and support structures were generated. The resin bath of the printer was heated to 35-40° C. before photopolymerization to reduce the viscosity to be able to manufacture the article. The following settings were used: Slice thickness=50 µm, Burn-In Layers=1, Separation Velocity=10 min/s, Slides per Layer=1, Burn-In Exposure Time=20.0 s, Normal Exposure Time=4 s. The photopolymerized aligners were then cleaned in isopropanol to remove unreacted resin and then post-cured under fusion lamps for 90 minutes on each side. The photopolymerized aligners fit the models, showing precision of the additive manufacture part. The aligners also had acceptable strength and flexibility.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. A photopolymerizable composition comprising a blend of:
   a. 1 to 80 wt. %, inclusive, of at least one polypropylene oxide component based on the total weight of the photopolymerizable composition, wherein the at least one polypropylene oxide component is of any of Formula VII, Formula VIII, Formula IX, Formula X, Formula XI, or Formula XII:

(VII)

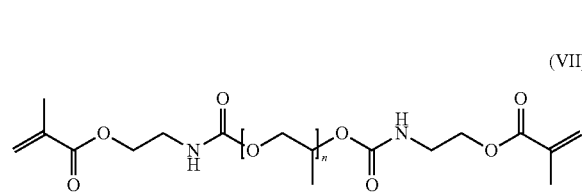

wherein n is 5 to 70;

(VIII)

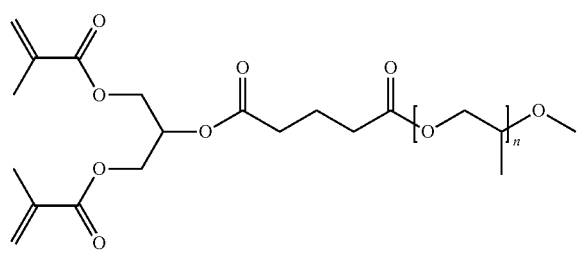

wherein n is 5 to 70 or 5 to 40;

(IX)

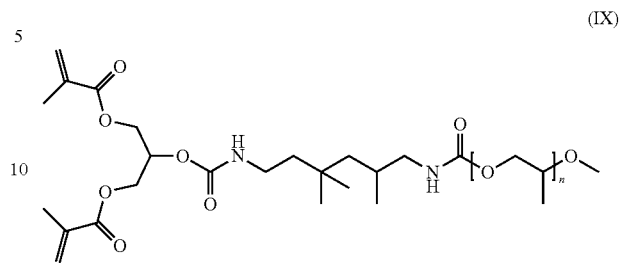

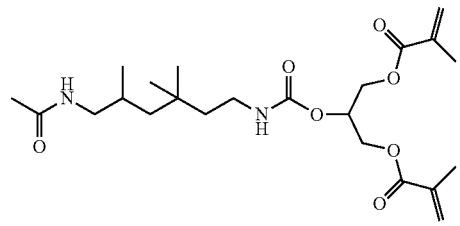

wherein n is 5 to 70 or 15 to 20;

(X)

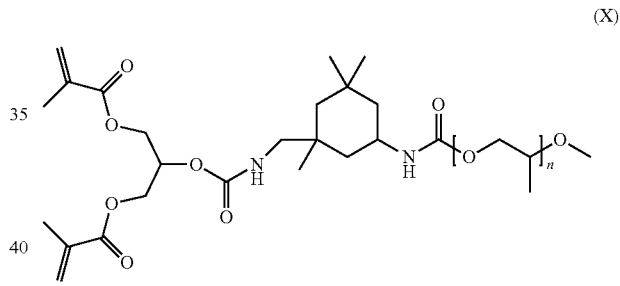

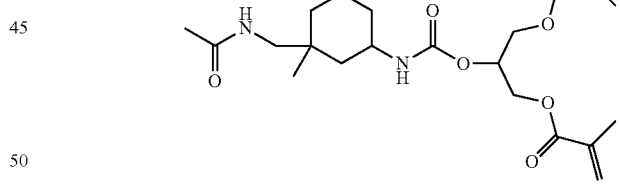

wherein n is 5 to 70 or 15 to 20;

(XI)

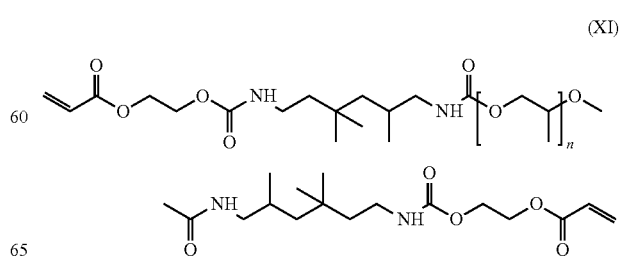

wherein n is 5 to 70 or 15 to 20; or (XII)

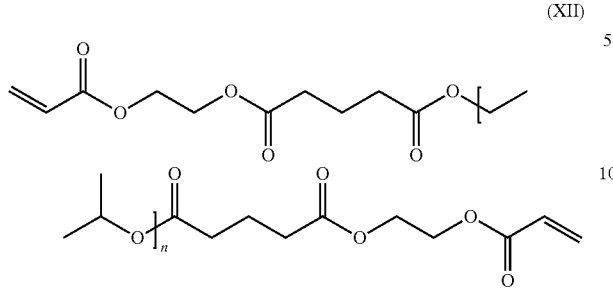

n is 5 to 70 or 15 to 20;
b. optionally 30 wt. % or greater of at least one urethane component, if present, based on the total weight of the photopolymerizable composition;
with the proviso that when the at least one urethane component is not present then the at least one polypropylene oxide component is of Formulae IX, X, or XI, and
with the proviso that when the at least one polypropylene oxide component is of Formula VII, then the at least one urethane component is present;

c. optionally at least one multifunctional reactive diluent in an amount of 1 to 30 wt. %, inclusive, if present, based on the total weight of the photopolymerizable composition;
d. 0.1 to 5 wt. %, inclusive, of at least one initiator; and
e. an optional inhibitor in an amount of 0.001 to 1 wt. %, inclusive, if present, based on the total weight of the photopolymerizable composition.

2. The photopolymerizable composition of claim 1, wherein the at least one polypropylene oxide component is of Formula VII:

(VII)

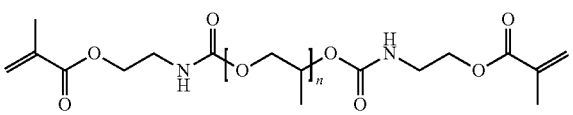

wherein n is 5 to 60.

3. The photopolymerizable composition of claim 1, wherein the at least one polypropylene oxide component is of Formula VIII:

(VIII)

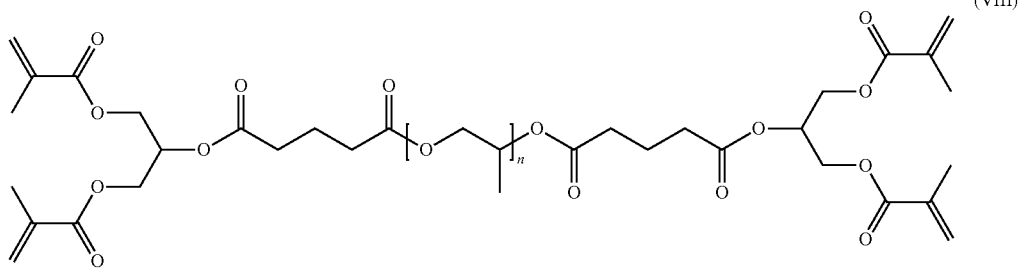

wherein n is 5 to 70 or 5 to 40.

4. The photopolymerizable composition of claim 1, wherein the at least one polypropylene oxide component is of Formula IX:

(IX)

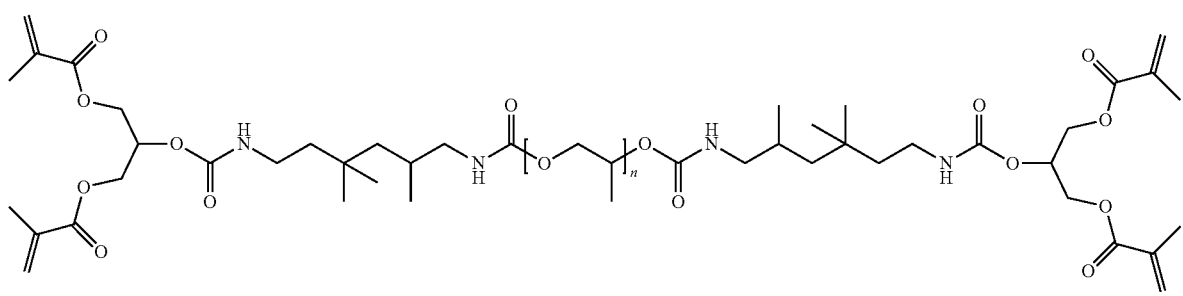

wherein n is 5 to 70 or 15 to 20.

5. The photopolymerizable composition of claim 1, wherein the at least one polypropylene oxide component is of Formula X:

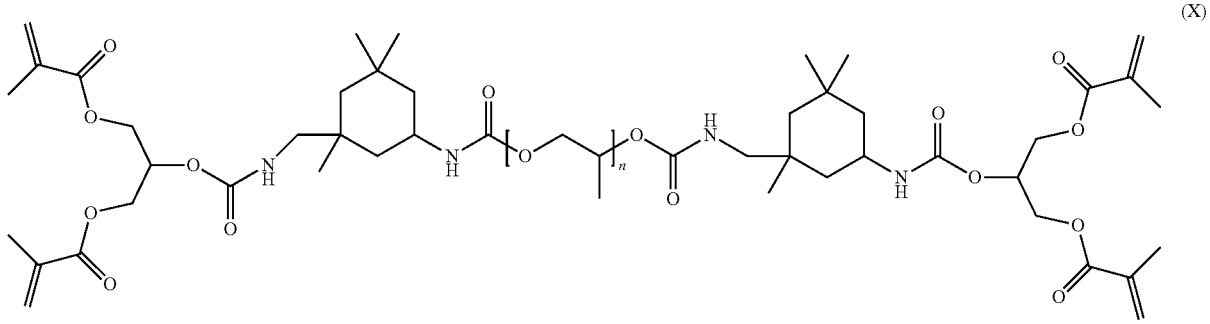

(X)

wherein n is 5 to 70 or 15 to 20.

6. The photopolymerizable composition of claim 1, wherein the at least one polypropylene oxide component is of Formula XI:

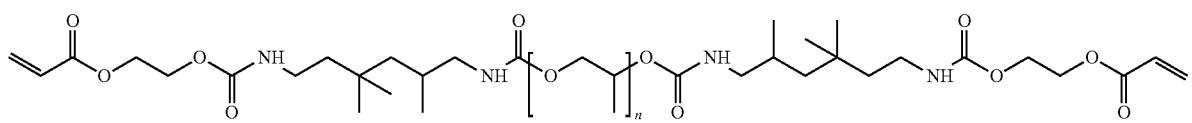

(XI)

wherein n is 5 to 70 or 15 to 20.

7. The photopolymerizable composition of claim 1, wherein the at least one polypropylene oxide component is of Formula XII:

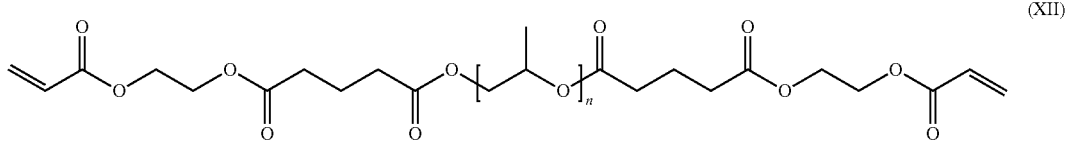

(XII)

wherein n is 5 to 70 or 15 to 20.

8. The photopolymerizable composition of claim 1, wherein the at least one multifunctional reactive diluent is present and comprises a polyester methacrylate.

9. The photopolymerizable composition of claim 1, wherein the polypropylene oxide segment has a molecular weight of 400 to 2,000 grams per mole (g/mol).

10. An article comprising a reaction product of a photopolymerizable composition of claim 1, wherein the article comprises an orthodontic article.

11. The article of claim 10, wherein the article comprises a plurality of layers.

12. The article of claim 10, exhibiting an elongation at break of 30% or greater.

13. A method of making an article, the method comprising:
　a. providing a photopolymerizable composition of claim 1;
　b. selectively curing the photopolymerizable composition to form an article; and
　c. optionally curing unpolymerized polypropylene oxide component, urethane component, and/or reactive diluent remaining after step (b).

14. The method of claim 13, further comprising (d) repeating steps (a) and (b) to form multiple layers and create the article having a three-dimensional structure prior to step (c).

15. A non-transitory machine readable medium comprising data representing a three-dimensional model of an article, when accessed by one or more processors interfacing with a 3D printer, causes the 3D printer to create an article comprising a reaction product of the photopolymerizable composition of claim 1.

16. A method comprising:
　a. receiving, by a manufacturing device having one or more processors, a digital object comprising data specifying a plurality of layers of an article; and
　b. generating, with the manufacturing device by an additive manufacturing process, the article based on the digital object, the article comprising a reaction product of the photopolymerizable composition of claim 1.

17. A system comprising:
　a. a display that displays a 3D model of an article; and
　b. one or more processors that, in response to the 3D model selected by a user, cause a 3D printer to create a physical object of an article, the article comprising a reaction product of the photopolymerizable composition of claim 1.

18. The photopolymerizable composition of claim 1, wherein the urethane component is a urethane (meth)acrylate or a urethane (meth)acrylate oligomer.

19. The photopolymerizable composition of claim 1, wherein the at least one polypropylene oxide component is present in an amount of at least 10 wt %.

20. The photopolymerizable composition of claim 1, comprising:
   a polypropylene oxide component of Formula VIII present in an amount of 10 wt % to 20 wt %; and
   at least one urethane (meth)acrylate or urethane (meth)acrylate oligomer.

* * * * *